United States Patent [19]

Bernardon

[11] Patent Number: 5,476,860
[45] Date of Patent: Dec. 19, 1995

[54] DIAROMATIC COMPOUNDS DERIVED FROM A SALICYLIC UNIT AND THEIR USE IN HUMAN AND VETERINARY MEDICINE AND IN COSMETICS

[75] Inventor: Jean-Michel Bernardon, Le Rouret, France

[73] Assignee: Centre International de Recherches Dermatologiques (CIRD Galderma), Valbonne, France

[21] Appl. No.: 140,171

[22] Filed: Dec. 8, 1993

[30] Foreign Application Priority Data

May 13, 1991 [FR] France .................... 91 05747

[51] Int. Cl.$^6$ ............... A61K 31/445; A61K 31/19; C07C 65/11; C07D 211/32
[52] U.S. Cl. ............ 514/319; 514/237.5; 514/456; 514/469; 514/510; 514/539; 514/546; 514/562; 514/567; 514/569; 514/618; 514/620; 514/677; 514/681; 514/682; 514/700; 514/717; 514/719; 514/721; 514/732; 544/165; 544/173; 544/174; 546/205; 549/23; 549/398; 560/10; 560/46; 560/56; 560/66; 560/67; 562/427; 562/453; 562/466; 562/475; 564/162; 564/165; 564/171; 564/172; 568/44; 568/49; 568/326; 568/327; 568/441; 568/632; 568/633; 568/732; 424/401; 424/428
[58] Field of Search .............. 560/56, 66, 67; 562/466, 475; 564/171, 172; 546/205; 549/23; 568/49, 327, 441, 632, 633, 732; 514/319, 456, 546, 569, 620, 700, 732; 424/401, 428

[56] References Cited

U.S. PATENT DOCUMENTS 4,937,371 6/1990 Carson et al. ............... 560/53

FOREIGN PATENT DOCUMENTS 0154928 9/1985 European Pat. Off. .
2172868 10/1973 France .
1566497 4/1980 United Kingdom .

OTHER PUBLICATIONS

Carson et al, Chemical Abstracts, vol. 111 (1989) 153363.
CA Previews, 94:553188 (1994).
S. Strickland et al., "Structure-Activity Relationships of a New Series of Retinoidal Benzoic Acid Derivatives as Measured by Induction of Differentiation of Murine F9 Teratocarcinoma Cells and Human HL-60 Promyelocytic Leukemia Cells", *Cancer Research*, 43, pp. 5268–5272, Nov. 1983.
A. K. Verma et al., "Inhibition of 12–O–Tetradecanoylphorbol–13–acetate–induced Ornithine Decarboxylase Activity in Mouse Epidermis by Vitamin A Analogs (Retinoids)", *Cancer Research*, 38, pp. 793–801, Mar. 1978.
M. M. Goodman et al., "Human Keratinocyte X HeLa Hydrids for Detection of Keratinocyte Differentiation–Specific Antigens", *Models Dermatol.*, 1989, vol. 4, pp. 1–4.
J. M. Geiger et al., "Rat Vaginal Epithelium Assay for Screening Retinoids", *Pharmacol Skin.*, 1989, vol. 3, pp. 141–143.

Primary Examiner—Richard L. Raymond
Attorney, Agent, or Firm—Oliff & Berridge

[57] ABSTRACT

Diaromatic compounds, characterized in that they correspond to the following general formula:

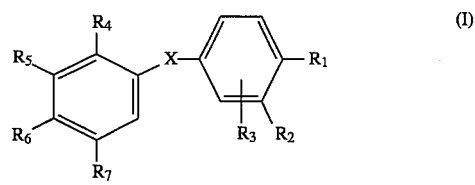

in which:

$R_1$ is —$CH_3$, —$CH_2OH$, —$COR_8$ or —$CH_2OCOR_9$, $R_8$ is H, OH, —$OR_{10}$, —N(rr') or alkyl, $R_{10}$ is alkyl, alkenyl, aryl or aralkyl, r and r' being H, alkyl, aryl, aralkyl, etc., r and r' together form a heterocycle, $R_9$ is alkyl, alkenyl or a sugar residue, $R_2$ and $R_3$ are —$OR_{11}$ or —$OCOR_{11}$, $R_{11}$ is H, alkyl, fluoroalkyl, aryl or aralkyl, $R_3$ in addition being H, $R_4$ is H, OH, alkyl, alkoxy, F, Cl or —$CF_3$, $R_5$ and $R_7$ are H, OH, alkoxy, α-substituted alkyl or α,α'-disubstituted alkyl, etc., $R_6$ is H, OH, alkyl, alkoxy, cycloalkyl, etc., $R_5$ and $R_7$ cannot simultaneously be OH or alkoxy and $R_4$, $R_5$, $R_6$ and $R_7$ cannot simultaneously be H, $R_5$ and $R_6$ or $R_6$ and $R_7$ can form, with the aromatic ring, a ring with 5 or 6 members, X is chosen from amongst:

(i) —$C(R_{13}R_{14})$—$C(R_{16}R_{18})$—W—, (ii) —$C(R_{14}R_{16})$—W—$C(R_{18}R_{19})$—, (iii) —$C(R_{13}R_{14})$—$C(R_{15}R_{16})$—$C(R_{18}R_{20})$—, (iv) —$CR_{17}$=$CR_{21}$—$C(R_{13}R_{14})$—, W is O, —$NR_{12}$ or $S(O)_n$, n=0, 1 or 2, $R_{13}$, $R_{15}$ and $R_{20}$ are H, —$OR_{11}$, —$OCOR_{11}$ etc., $R_{14}$, $R_{16}$, $R_{18}$ and $R_{19}$ are H, aralkyl, alkyl, etc., when X is (i) $R_{13}$ and $R_{14}$ can form =N—$OR_{11}$ or =N—$OCOR_{11}$, when X is (iii) or (iv), $R_{14}$, $R_{16}$ and $R_{18}$ are also —$OR_{11}$ or —$OCOR_{11}$, or $R_{13}$, $R_{14}$ or $R_{15}$, $R_{16}$ taken together can form =$NOR_{11}$ or =N—$OCOR_{11}$, $R_{12}$ is H, alkyl, aralkyl, alkenyl, alkynyl or fluoroalkyl, $R_{17}$ is H, hydroxyl, alkyl or alkoxy, $R_{21}$ is H or alkyl, and the salts of the compounds of formula (I).

18 Claims, No Drawings

DIAROMATIC COMPOUNDS DERIVED FROM A SALICYLIC UNIT AND THEIR USE IN HUMAN AND VETERINARY MEDICINE AND IN COSMETICS

FIELD OF THE INVENTION

This application is a 371 of PCT/FR92/00414, filed May 13, 1992.

The present invention relates to novel diaromatic compounds derived from a salicylic unit, a process for their preparation and their use in human and veterinary medicine and in cosmetics.

These novel compounds are used in the topical and systemic treatment of dermatological conditions connected with a disorder of keratinisation (differentiation/proliferation) and dermatological or other conditions with an inflammatory and/or immunoallergic component and in degenerative diseases of the connective tissue, and have an antitumour activity. In addition, these compounds can be used in the treatment of atopy, be it cutaneous or respiratory, and of rheumatoid psoriasis. They are also used in the ophthalmological field, especially in the treatment of corneopathies.

SUMMARY OF THE INVENTION

The compounds according to the invention can be represented by the following general formula:

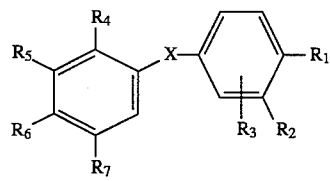

(I)

in which:

$R_1$ represents the —$CH_3$ radical, the —$CH_2OH$ radical, the —$COR_8$ radical or the —$CH_2OCOR_9$ radical, $R_8$ representing a hydrogen atom, OH, —$OR_{10}$,

or a lower alkyl radical, $R_{10}$ representing an alkyl radical having 1 to 20 carbon atoms, an alkenyl radical having 2 to 20 carbon atoms, or an aryl or aralkyl radical, r and r' identical or different, representing a hydrogen atom, a lower alkyl radical, an aryl radical, an aralkyl radical, an α-aminoacid residue, a sugar residue or a heterocycle or r and r' taken together forming a heterocycle, $R_9$ representing an alkyl radical having 1 to 20 carbon atoms, an alkenyl radical having 2 to 20 carbon atoms or a sugar residue, $R_2$ and $R_3$ represent —$OR_{11}$ or —$OCOR_{11}$ $R_{11}$ representing a hydrogen atom, a lower alkyl radical, a fluoroalkyl radical having 1 to 6 carbon atoms and 3 to 7 fluorine atoms, an aryl radical or an aralkyl radical, it being possible for $R_3$ to additionally represent a hydrogen atom, $R_4$ represents a hydrogen atom, OH, a lower alkyl radical, an alkoxy radical having 1 to 6 carbon atoms, a fluorine or chlorine atom or the —$CF_3$ group, $R_5$ and $R_7$ represent a hydrogen atom, OH, an alkoxy radical having 1 to 6 carbon atoms, an α-substituted alkyl radical having 3 to 12 carbon atoms or an α,α'-disubstituted alkyl radical having 4 to 12 carbon atoms, a cycloalkyl radical having 3 to 12 carbon atoms, a mono- or polycyclic radical having 5 to 12 carbon atoms connected to the phenyl ring by a tertiary carbon, it not being possible for $R_5$ and $R_7$ to simultaneously represent OH or alkoxy, $R_6$ represents a hydrogen atom, OH, a lower alkyl radical, an alkoxy radical having 1 to 6 carbon atoms, a cycloalkyl radical having 3 to 12 carbon atoms, a monohydroxyalkyl radical, a polyhydroxyalkyl radical, a fluorine atom, a chlorine atom, an alkenyl radical having 2 to 6 carbon atoms or an alkenyloxy radical having 2 to 6 carbon atoms, it not being possible for $R_4$, $R_5$, $R_6$ and $R_7$ to simultaneously represent a hydrogen atom, $R_5$ and $R_6$ or $R_6$ and $R_7$ taken together can form, together with the adjacent aromatic ring, a ring with 5 or 6 members optionally substituted by methyl groups and/or optionally interrupted by an oxygen or sulphur atom, X is a divalent radical which can be read from left to right or conversely, chosen amongst the group formed by:
(i) —$C(R_{13}R_{14})$—$C(R_{16}R_{18})$—W—
(ii) —$C(R_{14}R_{16})$—W—$C(R_{18}R_{19})$—
(iii) —$C(R_{13}R_{14})$—$C(R_{15}R_{16})$—$C(R_{18}R_{20})$—
(iv) —$CR_{17}$=$CR_{21}$—$C(R_{13}R_{14})$— in which:

W represents an oxygen atom, the —$NR_{12}$ group or the S(O)n group, n being 0, 1 or 2, $R_{13}$, $R_{15}$ and $R_{20}$ represent a hydrogen atom, the —$OR_{11}$, —$OCOR_{11}$, or —$NHCOR_{11}$ radical, an

radical, an aralkyl radical, a lower alkyl radical, a monohydroxyalkyl radical or a polyhydroxyalkyl radical, r" and r'", identical or different, representing a hydrogen atom, a lower alkyl radical, an alkenyl radical having 2 to 6 carbon atoms or an alkynyl radical having 2 to 6 carbon atoms, $R_{14}$, $R_{16}$, $R_{18}$ and $R_{19}$ represent a hydrogen atom, an aralkyl radical, a lower alkyl radical, or a monohydroxyalkyl or polyhydroxyalkyl radical, when X represents (i), $R_{13}$ and $R_{14}$ can form a group =N—$OR_{11}$ or a group =N—$OCOR_{11}$, and when X represents (iii) or (iv), $R_{14}$, $R_{16}$ and $R_{18}$ can also represent the —$OR_{11}$ radical or the —$OCOR_{11}$ radical, oxo, or else $R_{13}$, $R_{14}$ or $R_{15}$, $R_{16}$ taken together can fore a group =$NOR_{11}$ or a group =N—$OCOR_{11}$, $R_{12}$ representing a hydrogen atom, a lower alkyl radical, an aralkyl radical, an alkenyl radical having 2 to 6 carbon atoms, an alkynyl radical having 2 to 6 carbon atoms or a fluoroalkyl radical having 1 to 6 carbon atoms and 3 to 7 fluorine atoms, $R_{17}$ representing a hydrogen atom, a hydroxyl group, a lower alkyl radical or an alkoxy radical having 1 to 6 carbon atoms, $R_{21}$ representing a hydrogen atom or a lower alkyl radical, and the salts of the compounds of formula (I) when $R_1$ represents a carboxylic acid function or when $R_{13}$, $R_{16}$ or $R_{20}$ represents an amine function, and the optical isomers of the compounds of formula (I).

DESCRIPTION OF PREFERRED EMBODIMENTS

When the compounds according to the invention are present in the form of salts, in the case where $R_1$ represents a carboxylic function these are salts of an alkali or alkaline earth metal or else of zinc or of an organic amine, in the case where $R_{13}$ or $R_{15}$ or $R_{20}$ represents an amine group these are pharmaceutically or cosmetically acceptable salts formed by addition of an inorganic or organic acid chosen from amongst hydrochloric, sulphuric, acetic, citric, fumaric, hemisuccinic, maleic and mandelic acid.

Lower alkyl radical is understood as meaning a radical having 1 to 6 carbon atoms and preferably the methyl, ethyl, isopropyl, butyl and tertiary butyl radicals.

Alkoxy radical having 1 to 6 carbon atoms may especially be understood as meaning a methoxy, ethoxy, isopropoxy or butoxy radical.

α-Substituted alkyl radical having 3 to 12 carbon atoms may especially be understood as meaning an isopropyl, 1-methylpropyl or 1-ethylpropyl radical.

α,α'-Disubstituted alkyl radical having 4 to 12 carbon atoms may especially be understood as meaning a tert-butyl, 1,1-dimethylpropyl, 1-methyl-1-ethylpropyl, 1-methyl-1-ethylhexyl or 1,1-dimethyldecyl radical.

Monohydroxyalkyl radical may be understood as meaning a radical having from 1 to 6 carbon atoms, especially a 2-hydroxyethyl, 2-hydroxypropyl or 3-hydroxypropyl radical.

Polyhydroxyalkyl radical may be understood as meaning a radical containing from 2 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue.

Aryl radical may be understood as meaning a phenyl radical optionally substituted by at least one halogen atom, one hydroxyl or one nitro function.

Aralkyl radical may be understood as meaning the benzyl or phenethyl radical optionally substituted by at least one halogen atom, one hydroxyl or one nitro function.

Cycloalkyl radical having 3 to 12 carbon atoms may be understood as meaning especially a cyclopentyl or cyclohexyl radical.

Mono- or polycyclic cycloalkyl radical having 5 to 12 carbon atoms of which the bonding carbon is trisubstituted can be understood as meaning the 1-methylcyclohexyl or 1-adamantyl radical.

Alkenyloxy radical having 2 to 6 carbon atoms may be understood as meaning linear or branched radicals, especially allyloxy and vinyloxy.

Alkenyl radical having 2 to 6 carbon atoms may be understood as meaning especially the vinyl, allyl or 2-butenyl radicals.

Alkynyl radical having 2 to 6 carbon atoms may be understood as meaning especially the propargyl radical.

Fluoroalkyl radical having from 1 to 6 carbon atoms and from 3 to 7 fluorine atoms is understood as meaning in particular the groups $CF_3$ and $C_2F_5$.

When $R_9$ or $R_{10}$ represents an alkyl radical having 1 to 20 carbon atoms or an alkenyl radical having from 2 to 20 carbon atoms these may be understood as meaning linear or branched radicals optionally substituted by one or more hydroxyl groups or one or more fluorine atoms.

Amino acid residue may be understood as meaning a residue derived, for example, from one of the 20 amino acids of L or D configuration (or their racemic mixture) constitutive of mammalian proteins.

Sugar residue may be understood as meaning a residue derived, for example, from glucose, galactose or mannose.

Heterocycle is preferably understood as meaning a piperidino, morpholino, pyrrolidino or piperazino radical, optionally substituted in position 4 by a $C_1$–$C_6$ alkyl or mono- or polyhydroxyalkyl radical such as defined above.

Among the compounds of formula (I) above, the following may especially be mentioned:

1) 2-hydroxy-4-[2-hydroxy-2-(5,6,7,8-tetrahydro-5,5,8,8-tetramethyl-2-naphthyl)ethoxy]benzoic acid;
2) methyl 2-hydroxy-4-[2-hydroxy-2-(5,6,7,8-tetrahydro-5,5,8,8-tetramethyl-2-naphthyl)ethoxy]benzoate;
3) 2-hydroxy-4-[2-hydroxyimino-2-(5,6,7,8-tetrahydro-5,5,8,8-tetramethyl-2-naphthyl)ethoxy]benzoic acid;
4) 2-acetoxy-4-[2-acetoxy-2-(5,6,7,8-tetrahydro-5,5,8,8-tetramethyl-2-naphthyl)ethoxy]benzoic acid;
5) 2-hydroxy-4-[2-acetoxy-2-(5,6,7,8-tetrahydro-5,5,8,8-tetramethyl-2-naphthyl)ethoxy]benzoic acid;
6) 2-acetoxy-4-[2-hydroxy-2-(5,6,7,8-tetrahydro-5,5,8,8-tetramethyl-2-naphthyl)ethoxy]benzoic acid;
7) 2-hydroxy-4-[2-(5,6,7,8-tetrahydro-5,5,8,8-tetramethyl-2-naphthyl)ethoxy]benzoic acid;
8) 2-hydroxy-4-[2-hydroxy-2-(5,6,7,8-tetrahydro-5,5,8,8-tetramethyl-2-naphthyl)ethoxy]benzyl alcohol;
9) acetate of 2-acetoxy-4-[2-hydroxy-2-(5,6,7,8-tetrahydro-5,5,8,8-tetramethyl-2-naphthyl)ethoxy]benzyl alcohol;
10) piperidinyl N-2-hydroxy-4-[2-hydroxy-2-(5,6,7,8-tetrahydro-5,5,8,8-tetramethyl-2-naphthyl)ethoxy]benzamide;
11) morpholinyl N-2-hydroxy-4-[2-hydroxy-2-(5,6,7,8-tetrahydro-5,5,8,8-tetramethyl-2-naphthyl)ethoxy]benzamide;
12) 2-hydroxy-4-[2-hydroxy-2-(5,6,7,8-tetrahydro-5,5,8,8-tetramethyl-2-naphthyl)ethoxy]benzamide;
13) N-ethyl-2-hydroxy-4-[2-hydroxy-2-(5,6,7,8-tetrahydro-5,5,8,8-tetramethyl-2-naphthyl)ethoxy]benzamide;
14) methyl 2-hydroxy-4-[2-hydroxy-2-(4,4-dimethylthiochroman-6-yl)ethoxy]benzoate;
15) 2-hydroxy-4-[2-hydroxy-2-(4,4-dimethylthiochroman-6-yl)ethoxy]benzoic acid;
16) 2-hydroxy-4-[3-hydroxy-3-(5,6,7,8-tetrahydro-5,5,8,8-tetramethyl-2-naphthyl)propyl]benzoic acid;
17) 2-hydroxy-4-[2-hydroxy-2-(3,5-di-tert-butyl-4-hydroxyphenyl)ethoxy]benzoic acid;
18) 2-hydroxy-4-[2-hydroxy-2-(5,6,7,8-tetrahydro-5,5,8,8-tetramethyl-2-naphthyl)ethoxy]toluene;
19) methyl 2,6-dihydroxy-4-[2-hydroxy-2-(5,6,7,8-tetrahydro-5,5,8,8-tetramethyl-2-naphthyl)ethoxy]benzoate;

20) 2-hydroxy-4-[2-hydroxy-2-(3-tert-butyl-4-methoxyphenyl)ethoxy]benzoic acid;
21) 2-hydroxy-4-[2-hydroxy-2-(3-tert-butyl-4-hydroxyphenyl)ethoxy]benzoic acid;
22) (−) isomer of 2-hydroxy-4-[2-hydroxy-2-(5,6,7,8-tetrahydro-5,5,8,8-tetramethyl-2-naphthyl)ethoxy]benzoic acid;
23) (+) isomer of 2-hydroxy-4-[2-hydroxy-2-(5,6,7,8-tetrahydro-5,5,8,8-tetramethyl-2-naphthyl)ethoxy]benzoic acid;
24) 2-hydroxy-4-[2-hydroxy-2(3-methoxy-5,6,7,8 -tetrahydro-5,5,8,8-tetramethyl-2-naphthyl)ethoxy]benzoic acid;
25) 2-methoxy-4-[2-hydroxy-2-(5,6,7,8 -tetrahydro-5,5,8,8-tetramethyl-2-naphthyl)ethoxy]benzoic acid;
26) 2-hydroxy-4-[2-hydroxy-2-(3-hydroxy-5,6,7,8-tetrahydro-5,5,8,8-tetramethyl-2naphthyl)ethoxy]benzoic acid;
27) 2-hydroxy-4-[2-amino-2-(5,6,7,8-tetrahydro-5,5,8,8-tetramethyl-2-naphthyl)ethoxy]benzoic acid;
28) 2-hydroxy-4-[2-hydroxy-2-(5,6,7,8 -tetrahydro-5,5,8,8-tetramethyl-2-naphthyl)propyloxy]benzoic acid;
29) 2-hydroxy-4-[2-hydroxy-2-(5,6,7,8 -tetrahydro-5,5,8,8-tetramethyl-2-naphthyl)hexyloxy]benzoic acid;
30) 2-hydroxy-4-[2-hydroxy-2-(5,6,7,8 -tetrahydro-5-5,8,8-tetramethyl-2-naphthyl)ethylamino]benzoic acid;
31) 2-hydroxy-4-[[2-hydroxy-2-[3-(1-adamantyl)-4-methoxyphenyl]ethoxy]]benzoic acid;
32) 2-hydroxy-4-[[2-[3-(1-adamantyl)-4-methoxyphenyl]ethoxy]]benzoic acid.

The present invention also relates to the processes for the preparation of the compounds of formulae (Ia), (Ib), (Ic), (Id) and (Ie) according to the reaction schemes described below:

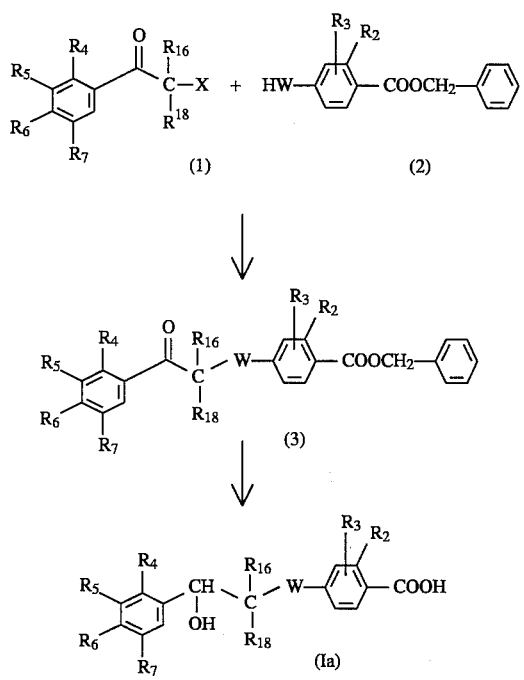

The first step of this preparation comprises reacting in anhydrous medium in an organic solvent such as DMF a haloketone (1) with a benzyl para-hydroxy-, para-amino- or para-thiosalicylate (2) in the presence of a tertiary amine (pyridine or triethylamine) or of an alkali metal hydride (sodium hydride) to obtain the compound of formula (3).

The principal step comprises hydrogenating the compound of formula (3) in the presence of a catalyst such as palladium on charcoal in an organic solvent such as dioxane, methanol or THF.

The hydrogenation can be carried out at a temperature between 20° and 60° C. under a hydrogen pressure of between 1 bar and 7 bars and at the same time allows the free acid to be obtained and the ketonic function to be reduced.

A hydroxyimino is obtained by the action of hydroxylamine on the compound (3). The reduction of the hydroxyimino allows the corresponding amine compound to be obtained.

The compounds of general formula (I) where X=(i) can also be prepared by reaction of an acid chloride (5) with an aromatic derivative (4) in the presence of a Lewis acid (for example $AlCl_3$) in a chlorinated solvent such as dichloromethane or dichloroethane or a nitrogenated solvent such as nitromethane or nitrobenzene. The ketone (6) thus obtained is reduced in alcohol with an alkali metal hydride such as $NaBH_4$ in an organic solvent such as THF or ethanol:

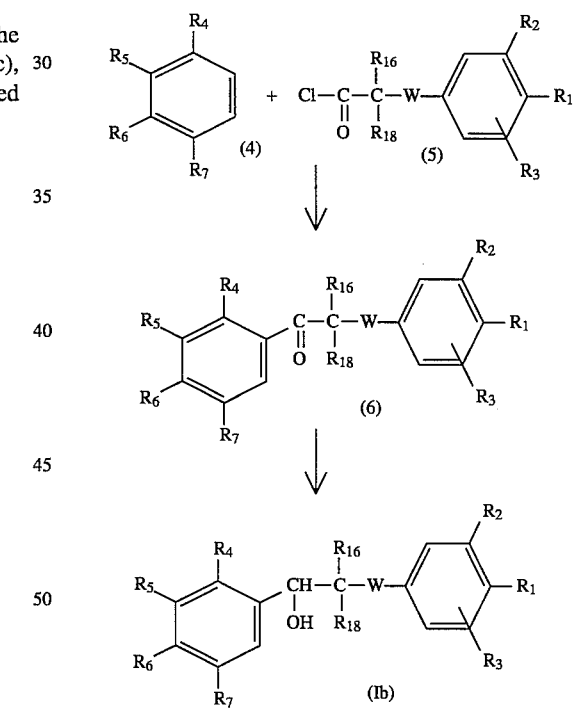

The compounds of general formula (I) where X=(ii) can be prepared by reaction of a substituted benzyl bromide (7) with a benzyl alcohol or a benzylamine or a substituted benzyl mercaptan (8) in the presence of pyridine or of a tertiary amine such as triethylamine in an organic solvent such as DMF or THF, or in the presence of an alkali metal carbonate, such as potassium carbonate, in a solvent such as acetone or methyl ethyl ketone.

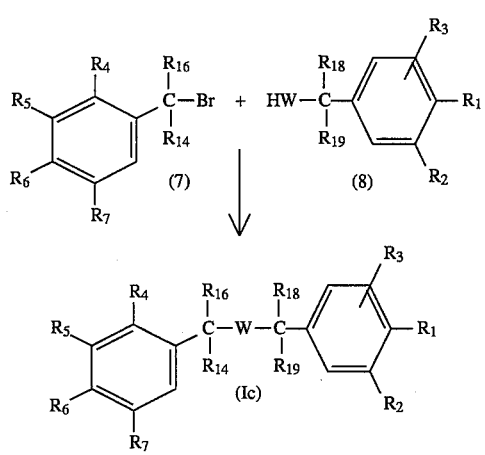

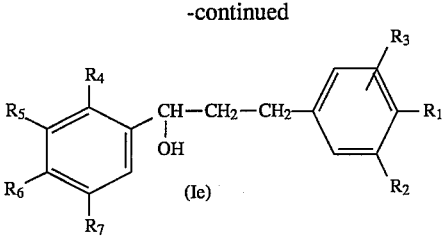

The compounds of general formula (I) where X=(iv) can be prepared by reaction of a substituted acetophenone (]) with a substituted benzaldehyde (10) in the presence of a base such as sodium hydroxide or sodium methoxide in an alcoholic solvent (ethanol). The chalcone (11) thus obtained is reduced in allyl alcohol (Id) with the aid of an alkali metal hydride such as $NaBH_4$ in an alcoholic solvent in the presence of a catalyst ($CeCl_3$).

Hydrogenation of the compound (Id) in the presence of a catalyst such as palladium on charcoal in a solvent such as dioxane or methanol gives compounds (Ie) of general formula (I) where X=(iii).

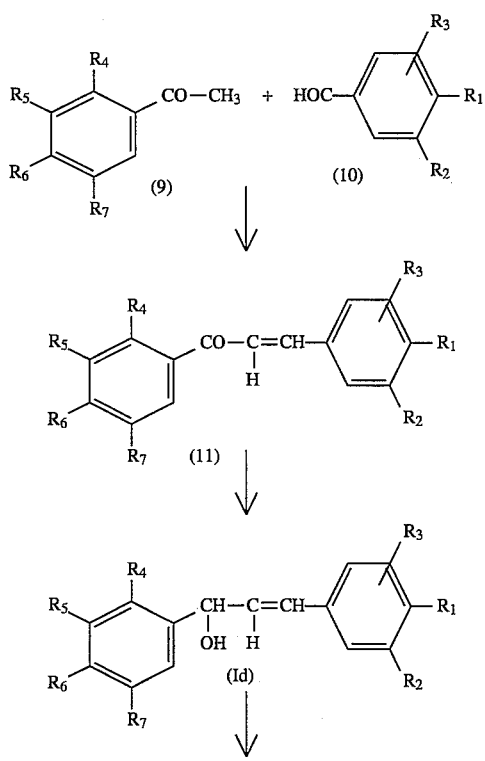

Mitsunobu-type reaction starting from the alcohols (Ib), (Id) or (Ie) gives the azido derivative which can converted into the amino derivative.

Reaction of an anhydride or of an acid chloride on the amino derivative gives the corresponding amide.

In the case where the radical X is read in the converse manner with respect to the above schemes resulting in the compounds (Ia), (Ib), (Id) or (Ie), the compounds are obtained by the reactions described in these schemes using starting materials having the appropriate substituents.

When, in the compounds according to the invention, X represents a di- or tri-hydroxyl radical, these are obtained by epoxidation of the corresponding ethylenic compounds and opening of the epoxy function in alkaline medium or in the presence of a hydride.

The present invention equally relates by way of medicament to the compounds of the formula (I) such as described above.

The compounds according to the invention have a good stability to light and to oxygen.

These compounds exhibit an activity in the embryonic teratocarcinoma cell (F9) differentiation test in the mouse (Cancer Research 43, p.5268, 1983) and/or in the ornithine decarboxylase inhibition test after induction by TPA in the mouse (Cancer Research 38, p.793–801, 1978) and/or on the differentiation of keratinocytes in man (Models Dermatol. Maibach HI, Lowe NJ Ed. Karger Basle (1989)) or in the female rat (Pharmacol. Skin 1989 Vol.3 P. 141–143). These tests show the activity of the compounds in the fields of differentiation and of proliferation. These compounds in addition have a good biological index.

The compounds according the invention are particularly well suited in the following areas of treatment:

1) For treating dermatological conditions connected with a disorder of keratinisation bearing on differentiation and on proliferation, especially for treating common, comedone or polymorphous acne, nodulocystic acne or acne conglobata, senile acne, and secondary acnes such as solar, drug and occupational acne.

2) For treating other types of keratinisation disorder, especially ichthyoses, ichthyosiform states, Darier's disease, palmoplantar keratodermias, leucoplasias and leucoplasiform states, or lichen, cutaneous or mucosal (buccal).

3) For treating other dermatological conditions connected with a disorder of keratinisation with an inflammatory and/or immunoallergic component and, especially, all forms of psoriasis, whether cutaneous, mucosal or unguinal, and even psoriatic rheumatism, or else cutaneous atopy, such as eczema or respiratory atopy or else gingival hypertrophy; the compounds can also be used in certain inflammatory conditions not showing a keratinisation disorder.

4) For treating all dermal or epidermal proliferations, whether benign or malignant, and whether of viral origin such as common warts, flat warts and verruciform epidermodysplasia, and oral or florid papillomas and proliferations which may also be induced by ultraviolet rays, especially in the case of basal and prickle cell epitheliomas.

5) For treating other dermatological disorders such as bullous dermatoses and collagen diseases.

6) For treating certain ophthalmological disorders, especially corneopathies.

7) For repairing or combating ageing of the skin, be it photoinduced or as a result of time or for reducing pigmentations and actinic keratoses.

8) For preventing or curing epidermal and/or dermal atrophy stigmata induced by local or systemic corticosteroids, or any other form of cutaneous atrophy.

9) For preventing or treating healing disorders or for preventing or repairing vergetures.

10) For combating disorders of the sebaceous function such as the hyperseborrhea of acne or simple seborrhea.

11) In the treatment of cancerous to precancerous states, in particular at the cutaneous level.

12) In the treatment of inflammatory conditions such as arthritis.

The present invention also relates to pharmaceutical compositions containing at least one compound of formula (I) such as defined above, or one of its salts.

The present invention thus also relates to a novel pharmaceutical composition intended especially for the treatment of the abovementioned conditions, characterised in that it contains, in a pharmaceutically acceptable carrier, at least one compound of formula (I) and/or one of its salts.

The compounds according to the invention are generally administered in a daily dose of approximately 0.01 mg/kg to 100 mg/kg of body weight in 1 to 3 doses.

Administration can be carried out by the enteral, parenteral, topical or ocular route. By the enteral route, the medicaments can be present in the form of tablets, gelatine capsules, coated tablets, syrups, suspensions, solutions, powders, granules, emulsions, microspheres or nanospheres or lipid or polymeric vesicles allowing a controlled release. By the parenteral route, the compositions can be present in the form of solutions or suspensions for perfusion or for injection.

By the topical route, the pharmaceutical compositions based on compounds according to the invention are intended for the treatment of the skin and of the mucosa and are present in the form of salved, creams, milks, ointments, powders, moistened pads, solutions, gels, sprays, lotions or suspensions. They can also be present in the form of microspheres or nanospheres or lipid or polymeric vesicles or polymeric patches and hydrogels allowing a controlled release.

These topical compositions can be present either in anhydrous form or in aqueous form according to the clinical indication.

By the ocular route, these are principally eye lotions.

These compositions contain at least one compound of formula (I) such as defined above or one of its salts, in a concentration preferably of between 0.001 and 5% with respect to the total weight of the composition.

The compounds of formula (I), according to the invention, are also used in the cosmetic field, in particular in body and hair hygiene and especially for the treatment of skins with a tendency to acne, for the regrowth of hair, against hair loss, for combating greasiness of the skin or of the hair, in protection against adverse effects of the sun or in the treatment of physiologically dry skins.

The present invention thus also aims at a cosmetic composition containing, in a cosmetically acceptable carrier, at least one compound of formula (I) or one of its salts, this composition especially being present in the form of a cream, a milk, a lotion, a gel, microspheres or nanospheres or lipid or polymeric vesiculas, a soap or a shampoo.

The concentration of the compound of formula (I) in the cosmetic compositions is between 0.001 and 3 % by weight.

The pharmaceutical and cosmetic compositions according to the invention may contain additives which are inert or even pharmacodynamically or cosmetically active, or combinations of these, and especially: wetting agents, depigmenting agents such as hydroquinone, azelaic acid, caffeic acid or kojic acid, emollients, hydrating agents such as glycerol, PEG 400, thiamorpholinone and its derivatives or urea; antiseborrheic or antiacne agents, such as S-carboxymethylcysteine, S-benzylcysteamine, their salts and their derivatives, tioxolone or benzoyl peroxide; antibiotics such as erythromycin and its esters, neomycin, chindamycin and its esters tetracyclines, antifungal agents such as ketoconazole or 4,5 -polymethylene-3-isothiazolinones; agents promoting the regrowth of the hair, such as "minoxidil" (2,4-diamino-6-piperidinopyrimidine-3-oxide) and its derivatives, diazoxide (7-chloro-3-methyl- 1,2,4-benzothiadiazine-1,1-dioxide) and phenytoin (5,5-diphenylimidazolidine-2,4-dione); steroidal and non-steroidal anti-flammatory agents; carotenoids and, especially, β-carotene; anti-psoriatic agents such as anthralin and its derivatives and eicosa-5,8,11,14-tetraynoic and eicosa-5,8,11-triynoic acids, their esters and amides.

The compositions according to the invention may also contain flavour-enhancing agents, preservatives such as the esters of para-hydroxybenzoic acid, stabilisers, humidity-regulating agents, pH-regulating agents, osmotic pressure-modifying agents, emulsifying agents, UV-A and UV-B filters, and antioxidants such as α-tocopherol, butylhydroxyanisole or butylhydroxytoluene.

Several examples of preparation of the active compounds of formula (I) according to the invention and also examples of compositions containing them will now be given by way of illustration and without any limiting character.

A. EXAMPLES OF COMPOUNDS

EXAMPLE 1

2-Hydroxy-4-[2-hydroxy,2-(5,6,7,8,-tetrahydro-5,5,8,8-tetramethyl-2-naphthyl)ethoxy]benzoic acid.

(a) Benzyl 2,4-dihydroxybenzoate:

15.4 g (0.1 mol) of 2,4-dihydroxybenzoic acid dissolved in 50 ml of DMF are added dropwise to a solution of 3 g (0.1 mol) of sodium hydride (80% in oil) and 50 ml of DMF and the mixture is stirred at room temperature until evolution of gas has ceased. 13.1 ml (0.1 mol) of benzyl bromide are then added and the mixture is stirred at room temperature until the reaction mixture has dissolved. The reaction mixture is poured into water and extracted with ethyl ether, and the organic phase is separated, washed with water, dried over magnesium sulphate and evaporated. The residue is purified by chromatography on a silica column, eluting with dichloromethane. 19.7 g (81%) of the expected ester are collected, which melts at 94°–95° C.

(b) 2-(2'-Bromoacetyl)-5,6,7,8-tetrahydro-5,5,8,8-tetramethylnaphthalene):

3.5 g (15.2 mmol) of 2-acetyl-5,6,7,8-tetrahydro-5,5,8, 8-tetramethylnaphthalene, 25 ml of ethyl ether and 25 ml of dioxane are introduced into a flask. 810 µl (15.2 mmol) of bromine are added dropwise and the mixture is stirred at room temperature for one hour. The reaction mixture is poured into water and extracted-with ethyl ether, and the organic phase is separated, dried over magnesium sulphate and evaporated. The residue obtained is purified by chromatography on a silica column, eluted with a mixture of dichloromethane and hexane (30–70). After evaporation of the solvents, 3.5 g (74%) of bromo derivative are collected, in the form of slightly yellow crystals, melting at 61°–62° C.

(c) Benzyl 2-hydroxy-4-(5,6,7,8-tetrahydro-5,5,8,8-tetramethyl-2-naphthoylmethoxy)benzoate:

300 mg (10 mmol) of sodium hydride (80% in oil) and 25 ml of DMF are introduced into a flask. A solution of 2.4 g (10 mmol) of benzyl 2,4-dihydroxybenzoate in 75 ml of DMF is added dropwise and the mixture is stirred until evolution of gas has ceased. A solution of 3.1 g (10 mmol) of the bromo derivative prepared above in 50 ml of DMF is then added and the mixture is stirred at room temperature for 2 hours. The reaction mixture is poured into water and extracted with ethyl ether, and the organic phase is separated, dried over magnesium sulphate and evaporated. The residue obtained is purified by chromatography on a silica column, eluted with a mixture of dichloromethane and hexane (50:50). After evaporation of the solvents, 3.4 g (73%) of the expected product are obtained, which melts at 103°–104° C.

(d) 2-Hydroxy-4-[2-hydroxy-2-(5,6,7,8-tetrahydro-5,5,8,8-tetramethyl-]2-naphthyl)ethoxy benzoic acid:

2.9 g (6.1 mmol) of the ester prepared above, 1 g of palladium on charcoal (10%) and 100 ml of dioxane are introduced into a reactor. The mixture is hydrogenated at room temperature and under a pressure of 7 bar for 4 hours, the catalyst is filtered and washed twice with 50 ml of THF each time, and the filtrates are evaporated. The residue obtained is purified by chromatography on a silica column, eluting with a mixture of dichloromethane and ethyl ether (95:5). After evaporation of the solvents, 2 g (87%) of 2-hydroxy-4-[2-hydroxy-2-(5,6,7,8-tetrahydro-5,5,8,8-tetramethyl-2-naphthyl)ethoxy-benzoic acid which melts at 206°–207° C. are collected.

EXAMPLE 2

Methyl 2-hydroxy-4-[2-hydroxy-2-(5,6,7,8-tetrahydro-5,5,8,8-tetramethyl-2-naphthyl)ethoxy]benzoate.

(a) Methyl 2-hydroxy-4-(5,6,7,8-tetrahydro-5,5,8-8-tetramethyl-2-naphthoylmethoxy)benzoate:

990 mg (33 mmol) of sodium hydride (80% in oil) and 50 ml of DMF are introduced in a flask. A solution of 5.6 g (33 mmol) of methyl 2,4-dihydroxybenzoate in 50 ml of DMF is added dropwise under a current of nitrogen and the mixture is stirred until evolution of gas has ceased. A solution of 9.4 g (33 mmol) of bromoketone prepared in 1(b) dissolved in 75 ml of DMF is then introduced dropwise and the mixture is stirred at room temperature for 2 hours. The reaction mixture is poured into water and extracted with ethyl ether, and the organic phase is separated, dried over magnesium sulphate and evaporated. The residue obtained is purified by chromatography on a silica column, eluted with a mixture of dichloromethane and hexane (70:30). After evaporation of the solvents, 8.5 g (72%) of the expected ester which melts at 113°–114° C. are collected.

(b) Methyl 2-hydroxy-4-[2-hydroxy-2-(5,6,7,8-tetrahydro-5,5,8,8-tetramethyl-2-naphthyl)ethoxy]benzoate:

1.6 g (4 mmol) of the ketone prepared above, 50 ml of THF and 50 ml of methanol are introduced into a flask. 80 mg (2 mmol) of sodium borohydride are added in small quantities and the mixture is stirred at room temperature for 2 hours. The reaction mixture is evaporated to dryness, the residue is taken up with water and ethyl ether, and the organic phase is separated, dried over magnesium sulphate and evaporated. The solid obtained is triturated in hexane, filtered and dried in vacuo. 1.6 g (100%) of the expected product which melts at 133°–134° C. are collected.

EXAMPLE 3

2-Hydroxy-4-[2-hydroxyimino-2-(5,6,7,8-tetrahydro-5,5,8,8-tetramethyl-2-naphthyl)ethoxy]benzoic acid (a) Methyl 2-hydroxy-4-[2-hydroxyimino-2-(5,6,7,8-tetrahydro-5,5,8,8-tetramethyl-2-naphthyl)ethoxy]benzoate.

6.6 g (16.6 mmol) of methyl 2-hydro-4-(5,6,7,8-tetrahydro-5,5,8,8-tetramethyl-2-naphthoylmethoxy) benzoate, 200 ml of ethanol and 4.6 g (66.6 mmol) of hydroxylamine hydrochloride are introduced into a flask. 66 ml of sodium hydroxide (iN) are added dropwise and the mixture is heated to reflux for 2 hours. It is evaporated to dryness, the residue is taken up with water and ethyl ether, and the organic phase is separated, dried over magnesium sulphate and evaporated. The residue obtained is purified by chromatography on a silica column, eluted with dichloromethane. After evaporation of the solvents, 4.4 g (64%) of the syn isomer which melts at 138°–9° C. and 1.9 g (30%) of the anti isomer which melts at 165°–166° C. are obtained.

(b) 2-Hydroxy-4-[2-hydroxyimino-2-(5,6,7,8-tetrahydro-5,5,8,8-tetramethyl-2-naphthyl)ethoxy]benzoic acid:

2.05 g (5 mmol) of the above syn isomer, 50 ml of THF and 50 ml of 2N methanolic sodium hydroxide are introduced into a flask. The mixture is heated to reflux for 8 hours, the reaction mixture is evaporated, the residue is taken up with water, and the mixture is neutralised with concentrated hydrochloric acid and extracted with ethyl ether. The organic phase is separated, dried over magnesium sulphate and evaporated. The residue obtained is triturated in dichloromethane and filtered. 1.6 g (81%) of the expected product which melts at 220°–222° C. with decomposition are obtained.

EXAMPLE 4

2-Acetoxy-4-[2-acetoxy-2-(5,6,7,8-tetrahydro-5,5,8,8-tetramethyl-2-naphthyl)ethoxy]benzoic acid (a) Benzyl 2-hydroxy-4-[2-hydroxy-2-(5,6,7,8-tetrahydro- 5,5,8,8-tetramethyl-2-naphthyl)ethoxy]benzoate.

5 g (10.5 mmol) of benzyl 2-hydroxy-4-(5,6,7,8-tetrahydro-5,5,8,8-tetramethyl-2-naphthoylmethoxy)benzoate, 50 ml of THF and 50 ml of methanol are introduced into a flask. 200 mg (5.3 mmol) of sodium borohydride are added in small quantities and the reaction mixture is stirred at room temperature for 1 hour. It is evaporated to dryness, the residue is taken up with water and ethyl ether, and the organic phase is separated, dried over magnesium sulphate and evaporated. 5 g (100%) of the expected product are collected in the form of a slightly yellow oil.

(b) Benzyl 2-acetoxy-4-[2-acetoxy-2-(5,6,7,8-tetrahydro-5, 5,8,8-tetramethyl-2-naphthyl)ethoxy]benzoate:

4.8 g (10 mmol) of the above product, 50 ml of THF and 4.2 ml (30 mmol) of triethylamine are introduced into a flask. 2.2 ml (30 mmol) of acetyl chloride are added dropwise and the reaction mixture is stirred at room temperature for 8 hours. It is poured into water and extracted with ethyl ether, and the organic phase is separated, dried over magnesium sulphate and evaporated. The residue obtained is purified by chromatography on a silica column, eluted with dichloromethane. After evaporation of the solvents, 3.8 g (76%) of the expected product are collected in the form of an oil.

(c) 2-Acetoxy-4-[2-acetoxy-2-(5,6,7,8 -tetrahydro-5,5,8,8-tetramethyl-2-naphthyl)ethoxy]benzoic acid:

1.5 g (2.7 mmol) of the above product, 200 ml of dioxane and 300 mg of Pd/C (10%) are introduced into a reactor. The mixture is hydrogenated at room temperature and under a pressure of 7 bar for 2 hours. The catalyst is filtered and washed twice with 50 ml of THF each time and the filtrates are evaporated. The residue obtained is triturated in a mixture of hexane and ethyl ether (90:10), filtered and dried in vacuo. 1.2 g (92%) of the expected product which melts at 88°–89° C. are collected.

EXAMPLE 5

2-Hydroxy-4-[2-acetoxy-2-(5,6,7,8-tetrahydro-5,5,8,8-tetramethyl1-2-naphthyl)ethoxy]benzoic acid (a) Benzyl 2-hydroxy-4-[2-acetoxy-(5,6,7,8 -tetrahydro-5,5,8,8-tetramethyl-2-naphthyl)ethoxy]benzoate 2.2 g (4.6 mmol) of benzyl 2-hydroxy-4-[2 -hydroxy-2-(5,6,7,8-tetrahydro-5,5,8,8-tetramethyl-2-naphthyl)ethoxy] benzoate, 50 ml of THF and 380 µl (4.6 mmol) of pyridine are introduced into a flask. 330 µl (4.6 mmol) of acetyl chloride are added dropwise and the reaction mixture is stirred at room temperature for 8 hours. It is poured into water and extracted with ethyl ether, and the organic phase is separated, dried over magnesium sulphate and evaporated. The residue obtained is purified by chromatography on a silica column, eluted with a mixture of hexane and dichloromethane (90:10). After evaporation of the solvents, 1.8 g (77%) of the expected product are collected in the form of a yellow oil.

(b) 2-Hydroxy-4-[2-acetoxy-2-(5,6,7,8 -tetrahydro-5,5,8,8-tetramethyl-2-naphthyl)ethoxy]benzoic acid Starting from 1.5 g (2.9 mmol) of the above product in a manner analogous to Example 4(c), 1.1 g (90%) of the expected product which melts at 160°–161° C. are obtained.

EXAMPLE 6

2-Acetoxy-4-[2-hydroxy-2,(5,6,7,8-tetrahydro-5,5,8,8-tetramethyl-2-naphthyl)ethoxy]benzoic acid (a) Benzyl 2-acetoxy-4-(5,6,7,8-tetrahydro-5,5,8,8-tetramethyl-2-naphthoylmethoxy)benzoate By reaction of 2.36 g (5 mmol) of benzyl 2-hydroxy-4-(5,6,7,8-tetrahydro-5,5,8,8-tetramethyl-2-naphthoylmethoxy)benzoate and 360 µl (5 mmol) of acetyl chloride in a manner analogous to Example 4(b), 2 g (80%) of the expected product which melts at 137°–138° C. are collected.

(b) 2-Acetoxy-4-[2-hydroxy-2-(5,6,7,8 -tetrahydro-5,5,8,8-tetramethyl-2-naphthyl)ethoxy]benzoic acid Starting from 1.9 g (3.7 mmol) of the above product in a manner analogous to Example 1(d), 1.4 g (89%) of the expected product which melts at 119°–120° C. are obtained.

EXAMPLE 7

2-Hydroxy-4-[2-(5,6,7,8-tetrahydro-5,5,8,8 -tetramethyl-2-naphthyl)ethoxy]benzoic acid 2 g (3.89 mmol) of benzyl 2-hydroxy-4-[2 -acetoxy-2-(5,6,7,8-tetrahydro-5,5,8,8-tetramethyl-2-naphthyl)ethoxy] benzoate obtained in Example 5(a), 100 ml of ethanol, 10 ml of acetic acid and 1.2 g of palladium on charcoal (10% to 50% water) are introduced into a reactor. The mixture is hydrogenated at 70° C., under a pressure of 7 bar, for 4 hours. The catalyst is filtered and washed with ethanol, and the filtrate is evaporated. The residue obtained is taken up in hexane, filtered and dried. 650 mg (46%) of the expected product of melting point 210°–212° C. are obtained.

EXAMPLE 8

2-Hydroxy-4-[2-hydroxy-2-(5,6,7,8-tetrahydro-5,5,8,8-tetramethyl-2-naphthyl)ethoxy]benzyl alcohol 1.27 g (2.68 mmol) of benzyl 2-hydroxy-4-(5,6,7,8-tetrahydro-5,5,8,8-tetramethyl-2-naphthyl)ethoxy]benzoate and 15 ml of THF are introduced into a flask. 480 mg (12 mmol) of LiAlH$_4$ (96%) are added in small quantities. The mixture is stirred at room temperature for 15 minutes. Hydrated Na$_2$SO$_4$ is added in small quantities. The mixture is stirred at room temperature overnight. The insoluble matter is filtered, and the filtrate is washed with THF and evaporated. The residue obtained is purified by chromatography on a silica column, eluted with a hexane/ethyl acetate mixture (60:40). After evaporation of the solvents, 260 mg (26%) of the expected product are collected in the form of a oil which crystallises slowly at room temperature, of melting point 110°–115° C.

EXAMPLE 9

2-Acetoxy-4-[2-hydroxy-2-(5,6,7,8-tetrahydro-5,5,8,8-tetramethyl-2-naphthyl)ethoxy]benzyl alcohol acetate 1.2 g (3.23 mmol) of 2-hydroxy-4-[2-hydroxy-2-(5,6,7,8-tetrahydro-5,5,8,8-tetramethyl-2naphthyl)ethoxy]benzyl alcohol and 30 ml of pyridine are introduced into a flask and 345 ml (4.84 mmol) of acetyl chloride are added. The reaction mixture is stirred at 0° C. for 4 hours. It is poured into water, acidified with hydrochloric acid and extracted with ethyl acetate. The extract is washed with water, and the organic phase is separated, dried over sodium sulphate and evaporated. The residue obtained is purified by chromatography on a silica column, eluted with a mixture of hexane and ethyl acetate (70:30). After evaporation of the solvents, 140 mg (10.4%) of the expected product are collected in the form of a pale yellow oil.

EXAMPLE 10

N-piperidinyl-2-hydroxy-4-[2-hydroxy-2-(5,6,7,8-tetrahydro-5,5,8,8-tetramethyl-2-naphthyl)ethoxy]benzamide 3.43 g (7.6 mmol) of N-piperidinyl-2-hydroxy-4-(5,6,7,8-tetrahydro-5,5,8,8-tetramethyl-2-naphthoylmethoxy)benzamide, 100 ml of isopropanol and 50 ml of THF are introduced into a flask. The mixture is cooled to 0° C. and 144 mg (3.81 mmol) of NaBH$_4$ are added. The mixture is stirred at 0° C. for 1 hour. Acetone is added, the solvents are evaporated, the residue is taken up in water and the mixture

EXAMPLE 11

N-Morpholinyl1-2-hydroxy-4-[2-hydroxy-2-(5,6,7,8-tetrahydro-5,5,8,8-tetramethyl-2-naphthyl)ethoxy]benzamide Starting from 5.5 g (12 mmol) of N-morpholinyl-2-hydroxy-4-(5,6,7,8-tetrahydro-5,5,8,8-tetramethyl-2-naphthoylmethoxy)benzamide in a manner analogous to Example 10 and by recrystallisation in 10 volumes of ethanol, 4.24 g (77%) of the expected product of melting point 153° C. are collected.

EXAMPLE 12

2-Hydroxy-4-[2-hydroxy-2-(5,6,7,8,tetrahydro-5,5,8,8-tetramethyl-2-naphthyl)ethoxy]benzamide Starting from 4.4g (11 mmol) of 2-hydroxy-4-(5,6,7,8-tetrahydro-5,5,8,8-tetramethyl-2-naphthoylmethoxy)benzamide in a manner analogous to Example 10, a yellow oil is obtained which crystallises in a mixture of ethanol/water. After filtration and drying, 3.72 g (84%) of the expected product of melting point 85°–90° C. are collected.

EXAMPLE 13

N-Ethyl-2-hydroxy-4-[2-hydroxy-2-(5,6,7,8-tetrahydro-5,5,8,8-tetramethyl-2-naphthyl)ethoxy]benzamide Starting from 2.4 g (5.87 mmol) of N-ethyl-2-hydroxy-4-(5,6,7,8-tetrahydro-5,5,8,8-tetramethyl-2-naphthoylmethoxy)benzamide in a manner analogous to Example 10, a yellow oil is obtained which crystallises in hexane. After filtration and drying, 2.24 g (93%) of the expected product of melting point 65°–70° C. are collected.

EXAMPLE 14

Methyl 2-hydroxy-4-[2-hydroxy-2-(4,4-dimethylthiochroman-6-yl)ethoxy]benzoate a) 6-(2-Bromoacetyl)-4,4-dimethylthiochroman In a manner analogous to Example 1(b), the synthesis is carried out starting from 1 g (4.42 mmol) of 6-acetyl-4,4-dimethylthiochroman and 700 mg (4.42 mmol) of bromine. After treatment and purification by chromatography on a silica column, eluting with a mixture of dichloromethane/hexane (40:60), 700 mg (53%) of expected bromo derivative are obtained in the form of a chestnut-brown oil.

b) Methyl 2-hydroxy-4-(4,4-dimethylthiochroman-6-oylmethoxy)benzoate 5 ml of dimethylformamide and 80 mg (2.75 mmol) of 80% sodium hydride are poured into a 100 ml three-necked flask, under nitrogen. 430 mg (2.57 mmol) of methyl 2,4-dihydroxybenzoate dissolved in 20 ml of dimethyl-formamide are introduced dropwise at room temperature and the mixture is stirred until evolution of hydrogen has ceased.

is adjusted to pH 6–7 with hydrochloric acid (1N). The mixture is extracted with ethyl acetate, washed with water and dried over sodium sulphate, and the solvents are evaporated. The residue obtained is purified by chromatography on a silica column eluted with a mixture of ethyl acetate and hexane (35:65). After evaporation of the solvents, the oil obtained is crystallised in hexane, filtered and dried, and 4.25 g (86%) of the expected product of melting point 124° C. are collected.

770 mg (2.57 mmol) of bromo derivative obtained above dissolved in 15 ml of dimethylformamide are then added. The mixture is stirred at room temperature for 5 hours, poured into water and extracted with ethyl ether, and the extract is dried over sodium sulphate. After filtration, the solvents are evaporated and 1 g of crude product is recovered which is chromatographed on a silica column, eluting with dichloromethane. 540 mg (53%) of expected product of melting point 135°–137° C. are thus obtained.

c) Methyl 2-hydroxy-4-[2-hydroxy-(4,4-dimethylthiochroman-6-yl)ethoxy]benzoate 540 mg (1.4 mmol) of the derivative obtained above dissolved in 15 ml of THF are introduced into a 50 ml"three-necked flask, under nitrogen. 50 mg (1.4 mmol) of sodium borohydride are added. After reacting for 30 minutes at room temperature, the reaction mixture is poured into water and extracted with ethyl acetate, the extract is dried over sodium sulphate and filtered, and the organic phase is evaporated to dryness. 530 mg of expected product, crystallising in hexane, of melting point 113°–115° C. are obtained.

EXAMPLE 15

2-hydroxy-4-[2-hydroxy-2-(4,4-dimethylthiochroman-6-yl)ethoxy]benzoic acid 450 mg (1.16 mmol) of the above derivative and 10 ml of methanol are introduced into a 100 ml flask, and 460 mg (11.6 mmol) of sodium hydroxide are added as pellets. The mixture is heated under reflux for 12 hours, the solvent is evaporated and the residue is taken up with water. The mixture is acidified and extracted with ethyl acetate, and the organic phase is dried over sodium sulphate, filtered and evaporated to dryness. 500 mg of a chestnut-brown oil are recovered, which is chromatographed on a silica column, eluting with ethyl acetate. After evaporation of the solvent, the residue is triturated in hexane and filtered. 210 mg (49%) of expected acid of melting point 166°–167° C. are thus obtained.

EXAMPLE 16

2-Hydroxy-4-[3-hydroxy-3-(5,6,7,8-tetrahydro-5,5,8,8-tetramethyl-2-naphthyl)propyl]benzoic acid a) 2-Hydroxy-4-[3-oxo-3-(5,6,7,8-tetrahydro-5,5,8,8-tetramethyl-2-naphthyl)-1-propenyl]benzoic acid 2.3 g (10 mmol) of 2-aceto-5,6,7,7,8-tetrahydro-5,5,8,8-tetramethylnaphthone, 1.8 g (10 mmol) of methyl 2-hydroxy-4-formylbenzoate, 70 ml of methanol and 40 ml of sodium hydroxide (1N) are introduced into a flask. The mixture is stirred at room temperature for 24 hours and evaporated to dryness, the residue is taken up with water, the mixture is acidified with hydrochloric acid and extracted with ethyl ether, and the organic phase is separated, dried over sodium sulphate and evaporated. The residue is recrystallised in ethyl alcohol, and the crystals are filtered and dried. 1.5 g (41%) of the expected product of melting point 260°–261° C. are collected.

b) 2-Hydroxy-4-[3-hydroxy-3-(5,6,7,8-tetrahydro-5,5,8,8-tetramethyl-2-naphthyl)propyl]benzoic acid 1.5 g (4 mmol) of the above acid are hydrogenated at room temperature and under a pressure of 7 bar in 60 ml of dioxane in the presence of 550 mg of 10% palladium on charcoal for 4 hours. After filtration and evaporation of the filtrate, the residue obtained is triturated in hexane and filtered. 870 mg (57%) of the expected product of melting point 144°–145° C. are collected.

EXAMPLE 17

2-Hydroxy-4-[2-hydroxy-2-(3,5-di-tert-butyl1-4-hydroxyphenyl)ethoxy]benzoic acid a) 3,5-Di-tert-butyl-4-hydroxy-2'-bromoacetophenone Starting from 2.5 g (10 mmol) of 3,5-di-tert-butyl-4-hydroxy-acetophenone, analogously to Example 1(b), 1.6 g (48%) of bromo derivative are collected in the form of a slightly yellow oil.

b) Benzyl 2-hydroxy-4-(3,5-di-tert-butyl-4-hydroxybenzoylmethoxy)benzoate

By reaction of 1.6 g (4.9 mmol) of the above bromo derivative with 1.2 g (4.9 mmol) of benzyl 2,4-dihydroxybenzoate in a manner analogous to Example 19(a), 2 g (83%) of the expected ester of melting point 122°–123° C. are obtained.

c) 2-Hydroxy-4-[(3,5-di-tert-butyl-4-hydroxybenzoyl)methoxy]benzoic acid 1.5 g (3.06 mmol) of the above ester, 60 ml of dioxane and 300 mg of 10% palladium on charcoal are introduced into a reactor. The mixture is hydrogenated at room temperature and under a pressure of 7 bar for 1 hour, the catalyst is filtered and the filtrate is evaporated. The residue obtained is triturated in hexane, filtered and dried. 1 g (82%) of the expected product of melting point 164°–165° C. is collected.

d) 2-hydroxy-4-[2-hydroxy-2-(3,5-di-tert-butyl-4hydroxyphenyl)ethoxy]benzoic acid Starting from 1 g (2.5 mmol) of the above ester in a manner analogous to Example 2(b), 710 mg (71%) of the expected product of melting point 132°–133° C. are obtained.

Example 18

2-Hydroxy-4-[2-hydroxy-2-(5,6,7,8-tetrahydro-5,5,8,8-tetramethyl-2-naphthyl)ethoxy]toluene a) 2-Hydroxy-4-(5,6,7,8-tetrahydro-5,5,8,8-tetramethyl-2-naphthoylmethoxy)benzaldehyde By reaction of 6.2 g (20 mmol) of 2'-bromoaceto)-5,6,7,8-tetrahydro-5,5,8,8-tetramethylnaphthone with 2.8 g (20 mmol) of 2,4-dihydroxybenzaldehyde in a manner analogous to Example 19(a), 6.9 g (94%) of expected aldehyde are obtained in the form of a colourless oil.

b) 2-hydroxy-4-[2-hydroxy-2-(5,6,7,8-tetrahydro-5,5,8,8-tetramethyl-2-naphthyl)ethoxy]toluene 1 g (2.7 mmol) of the above aldehyde is hydrogenated at room temperature and under a pressure of 7 bar in the presence of 200 mg of 10% palladium on charcoal. After filtration, and evaporation of the filtrate, the residue obtained is purified by chromatography on a silica column, eluting with a mixture of ethyl ether/hexane (30:70). 600 mg (62%) of the expected product of melting point 120°–121° C. are collected.

Example 19

Methyl 2,6-dihydroxy-4-[2-hydroxy-2-(5,6,7,8-tetrahydro-5,5,8,8-tetramethyl-2-naphthyl)ethoxy] benzoate a) Methyl 2,6-dihydroxy-4-(5,6,7,8-tetrahydro-5,5,8,8-tetramethyl-2-naphthoylmethoxy)benzoate 3.1 g (10 mmol) of 2-(2'-bromoaceto)-5,6,7,8-tetrahydro-5,5,8,8-tetramethylnaphthone, 1.8 g (10 mmol) of methyl 2,4,6-trihydroxybenzoate, 1.4 g (10 mmol) of potassium carbonate and 100 ml of methyl ethyl ketone are introduced into a flask. The mixture is heated under reflux for 1 hour and evaporated to dryness. The residue is taken up with water and dichloromethane, and the organic phase is separated, dried over magnesium sulphate and evaporated. The residue obtained is purified by chromatography on a silica column, eluted with a mixture of dichloromethane and hexane (50:50). After evaporation of the solvents, 2.2 g (53%) of the expected product of melting point 169°–170° C. are collected.

b) Methyl 2,6-dihydroxy-4-[2-hydroxy-2-(5,6,7,8-tetrahydro-5,5,8,8-tetramethyl-2-naphthyl)ethoxy]benzoate Starting from 2.7g (6.5 mmol) of the above ester in a manner analogous to Example 2(b), 2.1 g (77%) of the expected product of melting point 127°–128° C. are obtained.

EXAMPLE 20

2-Hydroxy-4-[2-hydroxy-2-(3-tert-butyl-4-methoxyphenyl)ethoxy]benzoic acid a) 3-tert-Butyl-4-methoxyacetophenone 22.6 g (0.1 mol) of 3-tert-butyl-4-methoxybenzoyl chloride, 30 ml of HMPA, 14 ml (0.1 mol) of tetramethyltin and 43 mg of benzyl(chloro)bis(triphenylphosphine)palladium(II) are introduced into a three-necked flask under a stream of nitrogen. The mixture is heated at 80° C. for 4 hours, poured into water and extracted with ethyl ether, and the organic phase is separated, dried over magnesium sulphate and evaporated. The residue obtained is purified by chromatography on a silica column, eluted with a mixture of dichloromethane/hexane (50:50). After evaporation of the solvents, 11.5 g (58%) of the expected ketone of melting point 68°–69° C. are collected.

b) 3-tert-Butyl-4-methoxy-(2'-bromo)acetophenone

Starting from 8.24 g (40 mmol) of the ketone obtained in 20(a), in a manner analogous to Example 1(b), 8.7 g (76%) of bromo derivative are obtained in the form of a slightly yellow oil.

c) Benzyl 2-hydroxy-4-[3-tert-butyl-4-methoxybenzoyl)methoxy]benzoate

By reaction of 8.7 g (30 mmol) of the above bromo derivative with 7.5 g (30 mmol) of benzyl 2,4-dihydroxybenzoate in a manner analogous to Example 19(a), 11 g (80%) of the expected ester of melting point 98°–99° C. are obtained.

d) 2-Hydroxy-4-[2-hydroxy-2-(3-tert-butyl-4-methyoxyphenyl)ethoxy]benzoic acid

Staring from 5 g (11.2 mmol) of ally 2-hydroxy-4-(3-tert-butyl-4-methoxybenzoylmethoxy)benzoate in a manner analogous to Example 1(d), 4 g (99%) of expected acid of melting point 149°–150° C. are obtained.

EXAMPLE 21

2-Hydroxy-4-[2-hydroxy-2-(3-tert-butyl-4-hydroxyphenyl)ethoxy]benzoic acid a) Methyl 3-tert-butyl-4-benzyloxybenzoate By reaction of 17 g (82 mmol) of methyl 3-tert-butyl-4-hydroxybenzoate with 10.7 ml (82 mmol) of benzyl bromide in a manner analogous to Example 1(a), 24.4 g (100%) of the expected product are obtained in the form of a colourless oil.

b) 3-tert-Butyl-4-benzyloxybenzoic acid 24.4 g (82 mmol)

of the above ester and 400 ml of 1N methanolic sodium hydroxide are introduced into a flask. The mixture is heated to reflux for 3 hours and evaporated to dryness, and the residue is taken up with water, acidified to pH=1 and extracted with ethyl ether, and the organic phase is separated, dried over magnesium sulphate and evaporated. The residue obtained is triturated in hexane, filtered and dried. 21 g (85%) of expected acid of melting point 213°–214° C. are collected.

c) 3-tert-butyl-4-benzyloxyacetophenone

By reaction of 10 g (35 mmol) of the above acid with 5 ml (35 mmol) of tetramethyltin in the presence of benzyl-(chloro)bis(triphenylphosphine(palladium(II) in a manner analogous to Example 20(a), 5.8 g (58%) of the expected ketone are obtained in the form of a colourless oil.

d) 3-tert-Butyl-4-methoxy-(2'-bromo)acetophenone

Starting from 5.8 g (20 mmol) of the ketone obtained in 21(c), in a manner analogous to Example 1(b), 4.6 g (62%) of the expected bromo derivative are obtained in the form of a slightly yellow oil.

e) Benzyl 2-hydroxy-4-[(3-tert-butyl-4-benzyloxybenzoyl-)methoxy]benzoate

By reaction of 4.6 g (13 mmol) of the above bromo derivative with 3.1 g (13 mmol) of benzyl 2,4 -dihydroxybenzoate in a manner analogous to Example 19(a), 5.4 g (81%) of the expected ester of melting point 91°–93° C. are obtained.

f) 2-Hydroxy-4-[2-hydroxy-2-(3-tert-butyl-4-hydroxyphenyl)ethoxy]benzoic acid

By hydrogenation of 2 g (3.8 mmol) of the above ester in the presence of 1.5 g of 10% palladium on charcoal in a manner analogous to Example 1(d), 1.9 g (90%) of the expected acid of melting point 96°–97° C. are obtained.

EXAMPLE 22

(−)-Isomer of 2-hydroxy-4-[2-hydroxy-2-(5,6,7,8-tetrahydro-5,5,8,8-tetramethyl-2-naphthyl)ethoxy]benzoic acid a) Benzyl 2-(2-methoxyethoxymethoxy)-4-(5,6,7,8-tetrahydro-5,5,8,8-tetramethyl-2-naphthoylmethoxy)benzoate 1.65 g (55 mmol) of sodium hydride (80% in oil) and 50 ml of DMF are introduced into a flask. A solution of 23.6 g (50 mmol) of allyl 2-hydroxy-4-(5,6,7,8-tetrahydro-5,5,8,8-tetramethyl-2-naphthoyl methoxy)benzoate in 200 ml of DMF is added dropwise and the mixture is stirred until evolution of gas has ceased. 6.3 ml (55 mmol) of 2-methoxy ethoxymethyl chloride are then added dropwise and the reaction mixture is stirred for 2 hours. It is poured into water and extracted with ethyl ether, and the organic phase is separated, dried over magnesium sulphate and evaporated. The residue obtained is purified by chromatography on a silica column, eluted with a mixture of dichloromethane/ethyl ether (98:2). After evaporation of the solvents, 19.2 g (69%) of the expected ester are collected in the form of a slightly yellow oil.

b) Benzyl 2-(2-methoxyethoxymethoxy)-4-( 2-hydroxy-2-(5,6,7,8-tetrahydro-5,5,8,8-tetramethyl-2-naphthyl)ethoxy] benzoate Starting from 10.3 g (18.3 mmol) of the above ester in a manner analogous to Example 2(b), 8.7 g (85%) of the expected product are obtained in the form of a yellow oil.

c) Benzyl 2(2-methoxyethoxymethoxy)-4-[2-(R)-α-methoxyphenylacetoxy-2-(5,6,7,8-teytrahydro-5,5,8,8tetramethyl-2-naphthyl)ethoxy]benzoate 10.5 g (18.6 mmol) of allyl 2-(2-methoxyethoxymethoxy)-4-(2-hydroxy-2-(5,6,7,8-tetrahydro- 5,5,8, 8-tetramethyl-2-naphthyl)ethoxy]benzoate, 3.1 g (18.6 mmol) of (R)-(−)-α-methoxyphenylacetic acid and 100 ml of dichloromethane are introduced into a flask. 3.8 g (18.6 mmol) of dicyclohexylcarbodiimide and 2.3 g (18.6 mmol) of 4-dimethylaminopyridine are added successively and the reaction mixture is stirred at room temperature for 4 hours. It is poured into water and extracted with ethyl ether, and the organic phase is separated, dried over magnesium sulphate and evaporated. The two diastereoisomers formed are separated by chromatography on a silica column, eluting with a mixture of hexane/ethyl ether (55:45). After evaporation of the solvents the following are collected:

5 g (38%) of the (−)-diastereoisomer in the form of a slightly yellow oil:

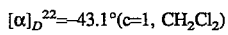

$[\alpha]_D^{22}=-43.1°(c=1, CH_2Cl_2)$ 4.8 g (36%) of the (+)-diastereoisomer in the form of a slightly yellow oil:

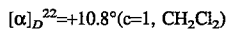

$[\alpha]_D^{22}=+10.8°(c=1, CH_2Cl_2)$ d) (−)-Diastereoisomer of benzyl 2-hydroxy-4-[2-(R)-α-methoxyphenylacetoxy-2-(5,6,7,8-tetrahydro-5,5,8,8-tetramethyl-2-naphthyl)ethoxy]benzoate 2.5 g (3.5 mmol) of the (−)-diastereoisomer prepared in Example 22(c) and 100 ml of dichloromethane are introduced into a flask. 270 mmol) of trifluoroacetic acid are added dropwise and the mixture is stirred for 15 min. It is poured into water and extracted with ethyl ether, and the organic phase is separated, dried over magnesium sulphate and evaporated. The residue is purified by filtration on silica, in a mixture of dichloromethane/hexane (90:10). After evaporation of the solvents, 2.1 g (97%) of the expected ester are collected in the form of a yellow oil:

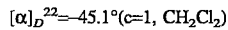

$[\alpha]_D^{22}=-45.1°(c=1, CH_2Cl_2)$ e) (−)-Isomer of 2-hydroxy-4-[2-hydroxy-2-(5,6,7,8-tetrahydro-5,5,8,8-tetramethyl-2-naphthyl)ethoxy]benzoic acid Starting from 2 g (3.2 mmol) of the above ester in a manner analogous to Example 3(c), 1.1 g (92%) of the expected (−)-acid of melting point 199°–200° C. are obtained.

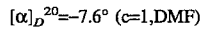

$[\alpha]_D^{20}=-7.6°(c=1,DMF)$

EXAMPLE 23

(+)-Isomer of 2-hydroxy-4-[2-hydroxy-2-(5,6,7,8-tetrahydro-5,5,8,8-tetramethyl-2-naphthyl)ethoxy]benzoic acid a) (+)-Diastereoisomer of benzyl 2-hydroxy-4-[2-(R)-α-methoxyphenylacetoxy-2(5,6,7,8-tetrahydro-5,5,8,8-tetramethyl-2-naphthyl)ethoxy]benzoate Starting from 4.4 g (6.3 mmol) of the (+)-diastereoisomer obtained in Example 22(c) in a manner analogous to Example 22(d), 3.7 g (95%) of the expected ester are collected in the form of a yellow oil:

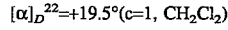

$[\alpha]_D^{22}=+19.5°(c=1, CH_2Cl_2)$ b) (+)-Isomer of 2-hydroxy-4-[2-hydroxy-2-(5,6,7,8-tetrahydro-5,5,8,8-tetramethyl-2-2-naphthyl)ethoxy]benzoic acid Staring from 3.5 g (5.6 mmol) of the above ester in a manner analogous to Example 22(e), 1.8 g (86%) of the expected (+)-acid of melting point 199°–200° C. are obtained:

$[\alpha]_D^{20} = +7.5°(c=1, DMF)$

EXAMPLE 24

2-Hydroxy-4-[2-hydroxy-2(3-methoxy-5,6,7,8-tetrahydro-5,5,8,8-tetramethyl-2-naphthyl)ethoxy]benzoic acid a) 3-Methoxy-5,6,7,8-tetrahydro-5,5,8,8-tetramethyl-2-acetonaphthone 990 mg (33 mmol) of sodium hydride (80% in oil) and 20 ml of DMF are introduced into a flask. A solution of 6.8 g (27.6 mmol) of 3-hydroxy-5,6,7,8-tetrahydro-5,5,8,8 -tetramethyl-2-acetonaphthone in 75 ml of DMF are added dropwise under a stream of nitrogen and the mixture is stirred until evolution of gas has ceased. 2.1 ml (33 mmol) of iodomethane are then added with cooling and the mixture is stirred at room temperature for 2 hours. It is then poured into water and extracted with ethyl ether, and the organic phase is separated, dried over magnesium sulphate and evaporated. The residue obtained is purified by chromatography on a silica column, eluted with a mixture of dichloromethane/hexane (40:60). After evaporation of the solvents, 6 g (84%) of the expected product of melting point 104°–105° C. are collected.

b) 2-(2'-Bromoaceto)-3-methoxy-5,6,7,8-tetrahydro-5,5,8,8-tetramethylnaphthone

Staring from 5.7 g (21.9 mmol) of the above ketone in a manner analogous to Example 1(b), 7.4 g (100%) of expected bromo derivative of melting point 99°–100° C. are obtained.

c) Benzyl 2-hydroxy-4-[3-methoxy-5,6,7,8-tetrahydro-5,5,8,8-tetramethyl-2-naphthoylmethoxy)benzoate By reaction of 7.4 g (21.9 mmol) of the above bromo derivative with 5.4 g (22 mmol) of benzyl 2,4-dihydroxybenzoate in a manner analogous to Example 19(a), 8.1 g (74%) of the expected ester of melting point 118°–119° C. are obtained.

d) 2-Hydroxy-4-(3-methoxy-5,6,7,8-tetrahydro-5,5,8,8-tetramethyl-2-naphthoylmethoxy)benzoic acid Starting from 1 g (2 mmol) of the above benzyl ester in a manner analogous to Example 18(c), 640 mg (78%) of the expected acid of melting point 200°–201° C. are obtained.

e) 2-Hydroxy-4-[2-hydroxy-2(3-methoxy-5,6,7,8-tetrahydro-5,5,8,8-tetramethyl-2-naphthyl)ethoxy]benzoic acid Staring from 1 g (2 mmol) of the above acid in a manner analogous to Example 2(a), 580 mg (70%) of the expected product of melting point 178°–179° C. are obtained.

EXAMPLE 25

2-Methoxy-4-[2-hydroxy-2-(5,6,7,8-tetrahydro-5,5,8,8-tetramethyl-2-naphthyl)ethoxy]benzoic acid a) Benzyl 2-methoxy-4-(5,6,7,8-tetrahydro-5,5,8,8-tetramethyl-2-naphthylmethoxy)benzoate By reaction of 1.9 g (4 mmol) of benzyl 2-hydroxy-4-(5,6,7,8-tetrahydro-5,5,8,8-tetramethyl-2-naphthoxylmethoxy)benzoate with 280 ml (4.4 mmol) of iodomethane in a manner analogous to Example 1(a), 1.8 g (93%) of the expected product of melting point 112°–113° C. are obtained.

b) 2-Methoxy-4-[2-hydroxy-2-(5,6,7,8 -tetrahydro-5,5,8,8-tetramethyl-2-naphthyl)ethoxy]benzoic acid Starting from 1.7 g (3.5 mmol) of the above benzyl ester in a manner analogous to Example 1(d), 1.1. g (79%) of the expected acid of melting point 150°–151° C. are obtained.

EXAMPLE 26

2-Hydroxy-4-[2-hydroxy-2-(3-hydroxy-5,6,7,8-tetrahydro-5,5,8,8-tetramethyl-2-naphthyl)ethoxybenzoic acid a) Benzyl 2-hydroxy-4(3-hydroxy-5,6,7,8,-teytrahydro-5,5,8,8-tetrameythyl-2-naphthoylmethoxy)benzoate 4 g (8 mmol) of benzyl 2-hydroxy-4-(3-methoxy-5,6,7,8,-tetrahydro-5,5,8,8-tetramethyl-2-naphthoxylmethoxy)benzoate and 20 ml of dichloromethane are introduced into a flask. 24 ml (24 mmol) of a solution of boron trichloride in THF (1M) are added dropwise at −78° C. and under a stream of nitrogen and the temperature is allowed to rise to −20° C., then the reaction mixture is poured into ice-water. The mixture is extracted with ethyl ether, and the organic phase is separated, dried over magnesium sulphate and evaporated. The residue obtained in purified by chromatography on a silica column, eluted with a dichloromethane/hexane mixture (50:50). 3.1 g (80%) of the expected ester of melting point 127°–128° C. are obtained.

b) 2-Hydroxy-4-(3-hydroxy-5,6,7,8-tetrahydro-5,5,8,8-tetramethyl-2-naphthoxylmethoxy)benzoic acid Starting from 2.8 g (5.7 mmol) of the above benzyl ester in a manner analogous to Example 17(c), 2 g (88%) of the expected acid which melts at 194°–195° C. are obtained.

c) 2-Hydroxy-4-[2-hydroxy-2-(3-hydroxy-5,6,7,8tetrahydro-5,5,8,8-tetramethyl-2-naphthyl)ethoxy]acid Starting from 1 g (2.5 mmol) of the acid obtained in 26(b) in a manner analogous to Example 2(b), 270 mg (27%) of expected acid of melting point 110°–111° C. are obtained.

EXAMPLE 27

2-Hydroxy-4-[2-amino-2-(5,6,7,8-tetrahydro-5,5,8,8-tetramethyl-2-naphthyl)ethoxy]benzoic acid a) Benzyl 2-hydroxy-4-[2-hydroxy-2-(5,6,7,8-tetrahydro-5,5,8,8-tetramethyl-2-naphthyl)ethoxy]benzoate Starting from 9.44 g (20 mmol) of benzyl 2-hydroxy-4-(5,6,7,8-tetrahydro-5,5,8,8-tetramethyl-2-naphthoylmethoxy)benzoate in a manner analogous to Example 2(b), 9/4 g (100%) of the expected ester are obtained in the form of a slightly yellow oil.

b) Benzyl 2-hydroxy-4-[2-methanesulphonyloxy-2-(5,6,7,8-tetrahydro-5,5,8,8-tetramethyl-2-naphthyl)ethoxy]benzoate 1.8 g (3.8 mmol) of the above ester, 920 ml (11.4 mmol) of pyridine and 100 ml of dichloromethane are introduced into a flask. A solution of 350 ml (4.6 mmol) of methanesulphonyl chloride in 50 ml of dichloromethane is added dropwise at 0° C. and the mixture is stirred at room temperature for 4 hours. It is evaporated to dryness, the residue is taken up with ethyl ether, and the organic phase is washed with water, dried over magnesium sulphate and evaporated. 2.1 g (100%) of the expected product are collected in the form of an oil.

c) Benzyl 2-hydroxy-4-[2-azido-2-(5,6,7,8 -tetrahydro-5,5,8,8-tetramethyl-2-naphthyl)ethoxy]benzoate 2.1 g (3.8 mmol) of the ester obtained in 27(b), 50 ml of DMF and 750 mg (11.4 mmol) of sodium azide are introduced into a flask. The reaction mixture is stirred at room temperature for 12 hours, poured into water and extracted with ethyl ether, and the organic phase is separated, dried over magnesium sulphate and evaporated. The residue obtained is purified by chromatography on a silica column, eluted with a dichloromethane/hexane mixture (40:60). After evaporation of the solvents, 1.2 g (67%) of the expected product are collected in the form of a colourless oil.

d) Benzyl 2-hydroxy-4-[2-amino-2-(5,6,7,8-tetrahydro-5,5,8,8-tetramethyl-2-naphthyl)ethoxy]benzoate 2.2 g (4.4 mmol) of the above ester, 1.2 g (4.4 mmol) of triphenylphosphine, 120 ml (6.6 mmol) of water and 100 ml of THF are introduced into a flask. The mixture is stirred at room temperature for 24 hours and evaporated to dryness, and the residue is chromatographed on a silica column eluting with a hexane/ethyl ether mixture (40:60). After evaporation of the solvents, 1 g (48%) of the expected product is collected in the form of a slightly yellow oil.

e) 2-Hydroxy-4-[2-amino-2-(5,6,7,8-tetrahydro-5,5,8,8-tetramethyl-2-naphthyl)ethoxy]benzoic acid 800 mg (1.7 mmol) of the above ester and 30 ml of a 2N methanolic sodium hydroxide solution are introduced into a flask. The reaction mixture is heated under reflux for 4 hours and evaporated, the residue is taken up with water, and the mixture is neutralised to pH=5 with 1N hydrochloric acid and extracted with ethyl ether. The organic phase is separated, washed with water, dried over magnesium sulphate and evaporated. The residue is triturated in the minimum of ethyl ether, filtered and dried. 110 g (17%) of the expected product of melting point 241°–242° C. are collected.

EXAMPLE 28

2-Hydroxy-4-[2-hydroxy-2-(5,6,7,8-tetrahydro-5,5,8,8-tetramethyl-2-naphthyl)propyloxy]benzoic acid 1 g (2.6 mmol) of 2-hydroxy-4-(5,6,7,8-tetrahydro-5,5,8,8-tetramethyl-2-naphthoylmethoxy)benzoic acid and 50 ml of THF are introduced into a three-necked flask under a stream of nitrogen. 5.3 ml (8.3 mmol) of a solution of methyl lithium in THF (1.6M) are added dropwise at −78° C. and the reaction mixture is stirred for 12 hours at room temperature. It is poured into ice-water, acidified to pH=1 and extracted with ethyl ether, and the organic phase is separated, dried over magnesium sulphate and evaporated. The residue obtained is recrystalised in cyclohexane and 900 mg (86%) of the expected product of melting point 170°–171° C. are collected.

EXAMPLE 29

2-Hydroxy-4-[2-hydroxy-2-(5,6,7,8-tetrahydro-5,5,8,8-tetramethyl-2-naphthyl)hexyloxy]benzoic acid By reaction of 1.1 g (2.9 mmol) of 2-hydroxy-4-(5,6,7,8-tetrahydro-5,5,8,8-tetramethyl-2-naphthylmethoxy)benzoic acid with 5.4 ml (8.6 mmol) of a solution of n-butyl-lithium (1.6M) in hexane in a manner analogous to Example 28, 140 mg (11%) of expected acid of melting point 142°–143° C. are obtained.

EXAMPLE 30

2-Hydroxy-4-[2-hydroxy-2-(5,6,7,8-tetrahydro-5,5,8,8-tetramethyl-2-naphthyl)ethylamino]benzoic acid 2.05 g (5 mmol) of methyl 2-hydroxy-4-(5,6,7,8-tetrahydro-5,5,8,8-tetramethyl-2-naphthoylcarboxamido)bezoate and 50 ml of dioxane are introduced into a flask. 1.9 g (50 mmol) of sodium borohydride are added in small quantities and the mixture is stirred for 30 min at room temperature. It is cooled to 0° C. and 2.9 ml (50 mmol) of acetic acid are added dropwise and the mixture is stirred for 4 hours at room temperature. It is poured into ice-water and extracted with ethyl ether, and the organic phase is separated, washed with water, dried over sodium sulphate and evaporated. The residue obtained is triturated in a hexane/ethyl ether mixture (50:50) filtered and dried. 1.7 g (89%) of 2-hydroxy-4-[2-hydroxy-2-(5,6,7,8-teytrahydro-5,5,8,8-tetramethyl-2-naphthyl)ethylamino]benzoic acid of melting point 165°–166° C. are collected.

EXAMPLE 31

2-Hydroxy-4-[[2-hydroxy-2-[3-(1-adamantyl)-4-methoxyphenyl]ethoxy]]benzoic acid 1.3 g (2.98 mmol) of 2-hydroxy-4-[[3-(1-adamantyl)-4-methoxybenzoyl]methoxy]benzoic acid, 200 mg of 10% palladium on charcoal and 50 ml of dioxane are introduced into a reactor. The mixture is hydrogenated at room temperature and under a pressure of 7 bar for 4 hours, the catalyst is filtered and washed with 50 of THF, and the filtrates are evaporated. The residue obtained is purified by chromatography on a silica column, eluting with a dichloromethane/methanol mixture (98:2). After evaporation of the solvents, 1 g (77%) of the expected acid of melting point 178°–179° C. is collected.

EXAMPLE 32

2-Hydroxy-4-[[2-[3-(1-adamantyl)-4-methoxyphenyl]ethoxy]]benzoic acid 1.3 g (2.98 mmol) of 2-hydroxy-4-[[3-(1-adamantyl)-4-methoxybenzoyl]methoxy]benzoic acid, 800 mg of 10% palladium on charcoal and 100 ml of dioxane are introduced into a reactor. The mixture is hydrogenated at room temperature under a pressure of 7 bar for 4 hours, the catalyst is filtered and washed with 50 ml of THF, and the filtrates are evaporated. The residue obtained is purified by chromatography on a silica column, eluting with a dichloromethane/methanol mixture (98:2). After evaporation of the solvents, 790 mg (60%) of the expected acid of melting point 210°–211° C. are obtained.

B. EXAMPLES OF FORMULATION

1) ORAL ROUTE a) 0.8 g tablet

Compound of Example 1 . . . 0.500 g
Pregelatinised starch . . . 0.100 g
Microcrystalline cellulose . . . 0.115 g
Lactose . . . 0.075 g
Magnesium stearate . . . 0.010 g In this example, the compound of Example 1 can be replaced by the same quantity of the compound of Example 23.

b) Drinkable suspension in 5 ml ampoules

Compound of Example 2 . . . 0.500 g
Glycerol . . . 0.500 g
70% sorbitol . . . 0.500 g
Sodium saccharinate . . . 0.010 g
Methyl para-hydroxybenzoate . . . 0.040 g
Flavouring q.s.
Purified water q.s.p. . . . 5 ml In this example, the compound of Example 2 can be replaced by the same quantity of the compound of Example 28.

(c) 0.2 g tablet
Compound of Example 3 . . . 0.001 g
Starch . . . 0.114 g
Bicalcium phosphate . . . 0.020 g
Silica . . . 0.020 g
Lactose . . . 0.030 g
Talc . . . 0.010 g
Magnesium stearate . . . 0.005 g In this example, the compound of Example 3 can be replaced by the same quantity of the compound of Example 15.

(d) Drinkable suspension in 10 ml amploules
Compound of Example 4 . . . 0.200 g
Glycerol . . . 1.000 g
70% sorbitol . . . 1.000 g
Sodium saccharinate . . . 0.010 g
Methyl para-hydroxybenzoate . . . 0.080 g
Flavouring q.s.
Purified water . . . q.s.p. . . . 10 ml (e) 0.5 q insoluble tablet
Compound of Example 5 . . . 0.050 g
Lactose . . . 0.082 g
Stearic acid . . . 0.003 g
Purified talc . . . 0.015 g
Sweetener . . . q.s.
Colorant . . . q.s.
Rice starch . . . q.s. . . . 0.500 g (f) 0.8 g insoluble tablet
Compound of Example 6 . . . 0.010 g
Lactose . . . q.s.p. . . . 0.800 g
20% gum arabic in water . . . 0.080 g
Liquid paraffin . . . 0.004 g
Purified talc . . . 0.016 g
Starch . . . q.s.p. . . . 0.800 g (g) 1 g capsules containing 0.5 g
Content of the capsule: Oily suspension
Content of Example 7 . . . 0.005 g
Paraffin oil . . . q.s.p. . . . 0.500 g The casing of the capsule is made by moulding and then drying an appropriate mixture composed of: gelatine, glycerol, water and preservative.

(h) Gelatine capsule containing 0.3 g of powder
Composition of the powder:
Compound of Example 14 . . . 0.100 g
Maize starch . . . 0.060 g
Lactose . . . q.s.p. . . . 0.300 g The powder is packed into a gelatine capsule composed of gelatine, TiO$_2$ and a preservative.

(i) 0.30 ml gelatine capsule
Opaque No. 3 standard calibre casing
Contents powder containing 0.1% by weight of active principle:
Compound of Example 17 . . . 0.3 mg
Magnesium stearate . . . 30 mg
Silica sold by the company DEGUSSA under the name Aerosil 200 . . . 30.0 mg
Lactose . . . q.s.p. . . . 0.3 ml

2—TOPICAL ROUTE (a) Non-ionic water-in-oil cream
Compound of Example 1 . . . 0.100 g
Mixture of emulsifying laolin alcohols, waxes and refined oils, sold by the company BDF under the name "Anhydrous Eucerine" . . . 39.900 g
Methyl para-hydroxybenzoate . . . 0.075 g
Propyl para-hydroxybenzoate . . . 0.075 g
Sterile demineralised water q.s.p. . . . 100 g In this example, the compound of Example 1 can be replaced by the same quantity of the compound of Example 8.

(b) Non-ionic oil-in-water cream
Compound of Example 2 . . . 1.000 g
Cetyl alcohol . . . 4.000 g
Glycerol monostearate . . . 2.500 g
PEG 50 stearate . . . 2.500 g
Karite butter . . . 9.200 g
Propylene glycol . . . 2.000 g
Methyl para-hydroxybenzoate . . . 0.075 g
Propyl para-hydroxybenzoate . . . 0.075 g
Sterile demineralised water q.s.p. . . . 100 g In this example, the compound of Example 2 can be replaced by the same quantity of the compound of Example 10.

(c) Lotion
Compound of Example 19 . . . 0.100 g
Polyethylene glycol (PEG 400) . . . 69.900 g
95% ethanol . . . 30.000 g In this example, the compound of Example 19 can be replaced by the same quantity of the compound of Example 21.

(d) Ointment
Compound of Example 20 . . . 0.020 g
Isopropyl myristate . . . 81.700 g
Liquid paraffin . . . 9.100 g
Silica sold by the company DEGUSSA under the name "Aerosil 200" . . . 9.180 g In this example, the compound of Example 20 can be replaced by the same quantity of the compound of Example 11.

(e) Ointment
Compound of Example 24 . . . 0.300 g
White petroleum jelly FP . . . q.s.p. . . . 100 g In this example, the compound of Example 24 can be replaced by the same quantity of the compound of Example 31.

(f) Hydrophobic ointment
Compound of Example 25 . . . 0.300 g
Isopropyl myristate . . . 36.400 g
Silicone oil sold by the company RHONE POULENC under the name "Rhodorsil 47 V 300" . . . 36.400 g
Beeswax . . . 13.600 g
Silicone oil sold by the company GOLDSCHMIDT under the name "Abil 300.000 cst" . . . q.s.p. . . . 100 g In this example, the compound of Example 25 can be replaced by the same quantity of the compound of Example 32.

(g) Hydrophilic ointment
Compound of Example 27 . . . 0.005 g
Anhydrous Eucerine . . . 60.000 g
Microcrystalline wax . . . 15.000 g
Liquid paraffin . . . q.s.p. . . . 100.000 g (h) Ointment
Compound of Example 22 . . . 0.050 g
Stearyl alcohol . . . 3.000 g
Lanolin . . . 5.000 g Petroleum jelly . . . 15.000 g
Distilled water . . . q.s.p. . . . 100.000 g
(i) Hydrophobic ointment
Compound of Example 26 . . . 1.000 g
Liquid paraffin . . . 9.100 g
Silica sold by the company DEGUSSA under the name Aerosil 200 . . . 9.180 g
Isopropyl myristate . . . q.s.p. . . . 100.000 g
(j) Anionic O/W cream
Compound of Example 30 . . . 0.050 g
Sodium dodecyl sulphate . . . 0.800 g
Glycerol . . . 2.000 g
Stearyl alcohol . . . 20.000 g
Triglyerides of capric/caprylic acids sold by the company DYNAMIT NOBEL under the name Miglyol 812 . . . 20.000 g
Preservatives . . . q.s.
Demineralised water . . . q.s.p. . . . 100.000 g
(k) Water-eliminable ointment
Compound of Example 29 . . . 0.500 g
PEG 400 . . . 50.500 g
PEG 4000 . . . 25.000 g
Liquid paraffin . . . 15.000 g

What is claimed is:

1. A diaromatic compound, having the following formula:

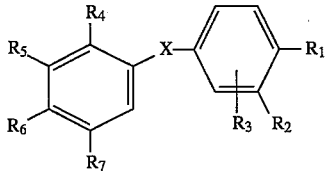

in which:

$R_1$ represents —$CH_3$, —$CH_2OH$, —$COR_8$ or —$CH_2OCOR_9$, $R_8$ representing a hydrogen atom, OH, —$OR_{10}$,

or a lower alkyl radical, $R_{10}$ representing an alkyl radical having 1 to 20 carbon atoms, an alkenyl radical having 2 to 20 carbon atoms, or an aryl or aralkyl radical, r and r', identical or different, representing a hydrogen atom, a lower alkyl radical, an aryl radical, an aralkyl radical, an α-aminoacid residue, a sugar residue or a heterocycle or r and r' taken together forming a heterocycle, $R_9$ representing an alkyl radical having 1 to 20 carbon atoms, an alkenyl radical having 2 to 20 carbon atoms or a sugar residue, $R_2$ represents —$OR_{11}$ or —$OCOR_{11}$ $R_3$ represents a hydrogen atom, —$OR_{11}$ or —$OCOR_{11}$ $R_{11}$ representing a hydrogen atom, a lower alkyl radical, a fluoroalkyl radical having 1 to 6 carbon atoms and 3 to 7 fluorine atoms, an aryl radical or an aralkyl radical, $R_4$ represents a hydrogen atom, OH, a lower alkyl radical, an alkoxy radical having 1 to 6 carbon atoms, a fluorine or chlorine atom or the —$CF_3$ group, $R_5$ and $R_6$ or $R_6$ and $R_7$ taken together form, with the adjacent aromatic ring, a ring with 5 or 6 members optionally substituted by methyl groups and optionally interrupted by an oxygen or sulphur atom, $R_5$ or $R_7$, whichever does not form the ring, is hydrogen, X is a divalent radical which from left to right or conversely is selected from the group consisting of:
(i) —$C(R_{13}R_{14})$—$C(R_{16}R_{18})$—W—, and
(ii) —$C(R_{13}R_{14})$—$C(R_{15}R_{16})$—$C(R_{18}R_{20})$— in which:

W represents an oxygen atom, —$NR_{12}$ or $S(S)_n$, n being 0, 1 or 2, $R_{13}$, $R_{15}$ and $R_{20}$ represent a hydrogen atom, —$OR_{11}$,

an aralkyl radical, a lower alkyl radical, a monohydroxyalkyl radical or a polyhydroxyalkyl radical, r" and r'", identical or different, representing a hydrogen atom, a lower alkyl radical, an alkenyl radical having 2 to 6 carbon atoms or an alkynyl radical having 2 to 6 carbon atoms, $R_{14}$, $R_{16}$ and $R_{18}$ represent a hydrogen atom, an aralkyl radical, a lower alkyl radical, or a monohydroxyalkyl or polyhydroxyalkyl radical, when X represents (i), $R_{13}$ and $R_{14}$ together can form a =N—$OR_{11}$ group or a =N—$OCOR_{11}$ group, and when X represents (ii) $R_{14}$, $R_{16}$ and $R_{18}$ can also represent —$OR_{11}$ or —$OCOR_{11}$ or $R_{13}$ and $R_{14}$ or $R_{15}$ and $R_{16}$ taken together can form a =$NOR_{11}$ group or a =N—$OCOR_{11}$ group, $R_{12}$ representing a hydrogen atom, a lower alkyl radical, an aralkyl radical, an alkenyl radical having 2 to 6 carbon atoms, an alkynyl radical having 2 to 6 carbon atoms or a fluoroalkyl radical having 1 to 6 carbon atoms and 3 to 7 fluorine atoms, or a salt of the compound of formula (I) when $R_1$ represents a carboxylic acid function or when $R_{13}$, $R_{16}$ or $R_{20}$ represents an amine function, or an optical isomer of the compound of formula (I).

2. The compound according to claim 1, wherein said compound is present in the form of a salt of an alkali metal or alkaline earth metal or of zinc or of an organic amine.

3. The compound according to claim 1, wherein said compound is present in the form of a salt of an inorganic or organic acid selected from the group consisting of hydrochloric, sulfuric, acetic, citric, fumaric hemisuccinic, maleic and mandelic acid.

4. The compound according to claim 1, wherein said lower alkyl radical is selected from the group consisting of methyl, ethyl, isopropyl, butyl and tertiary butyl.

5. The compound according to claim 1, wherein said alkoxy radical is selected from the group consisting of methoxy, ethoxy, isopropoxy and butoxy.

6. The compound according to claim 1, wherein said monohydroxyalkyl radical is selected from the group consisting of 2-hydroxy-ethyl, 2-hydroxypropyl and 3-hydroxypropyl.

7. The compound according to claim 1, wherein said polyhydroxyalkyl radical is selected from the group consisting of 2,3-dihydroxypropyl, 2,3,4-trihydroxybutyl, 2,3,4,5-tetrahydroxypentyl radical and pentaerythritol residue.

8. The compound according to claim 1, wherein said aryl radical is a phenyl radical optionally substituted by at least one halogen atom, hydroxyl or nitro function.

9. The compound according to claim 1, wherein said aralkyl radical is a benzyl or phenethyl radical optionally substituted by at least one halogen atom, hydroxyl, or nitro function.

10. The compound according to claim 1, wherein said alkynyl radical is propargyl.

11. The compound according to claim 1, wherein said alkenyl radical having 2 to 6 carbon atoms is selected from the group consisting of vinyl, allyl and 2-butenyl.

12. The compound according to claim 1, wherein said heterocycle is selected from the group consisting of piperidino, morpholino, pyrrolidino and piperazino, optionally substituted in 4 position by a $C_1$–$C_6$ alkyl or mono- or polyhydroxyalkyl radical.

13. The compound according to claim 1, wherein said compound is selected from the group consisting of:
2-hydroxy-4-[2-hydroxy-2-(5,6,7,8-tetrahydro-5,5,8,8-tetramethyl-2-naphthyl)ethoxy]benzoic acid;
methyl 2-hydroxy-4-[2-hydroxy-2-(5,6,7,8-tetrahydro-5,5,8,8-tetramethyl-2-naphthyl)ethoxy]benzoate;
2-hydroxy-4-[2-hydroxyimino-2-(5,6,7,8-tetrahydro-5,5,8,8-tetramethyl-2-naphthyl)ethoxy]benzoic acid;
2-acetoxy-4-[2-acetoxy-2-(5,6,7,8-tetrahydro-5,5,8,8-tetramethyl-2-naphthyl)ethoxy]benzoic acid;
2-hydroxy-4-[2-acetoxy-2-(5,6,7,8-tetrahydro-5,5,8,8-tetramethyl-2-naphthyl)ethoxy]benzoic acid;
2-acetoxy-4-[2-hydroxy-2-(5,6,7,8-tetrahydro-5,5,8,8-tetramethyl-2-naphthyl)ethoxy]benzoic acid;
2-hydroxy-4-]2-(5,6,7,8-tetrahydro-5,5,8,8-tetramethyl-2-naphthyl)ethoxy]benzoic acid;
2-hydroxy-4-[2-hydroxy-2-(5,6,7,8-tetrahydro-5,5,8,8-tetramethyl-2-naphthyl)ethoxy]benzyl alcohol;
acetate of 2-acetoxy-4-[2-hydroxy-2-(5,6,7,8-tetrahydro-5,5,8,8-tetramethyl-2-naphthyl)ethoxy]benzylalcohol;
N-piperidinyl-2-hydroxy-4-[2-hydroxy-2-(5,6,7,8-tetrahydro-5,5,8,8-tetramethyl-2-naphthyl)ethoxy]-benzamide;
N-morpholinyl-2-hydroxy-4-[2-hydroxy-2-(5,6,7,8-tetrahydro-5,5,8,8-tetramethyl-2-naphthyl)ethoxy]-benzamide;
2-hydroxy-4-[2-hydroxy-2-(5,6,7,8-tetrahydro-5,5,8,8-tetramethyl-2-naphthyl)ethoxy]benzamide;
N-ethyl-2-hydroxy-4-[2-hydroxy-2-(5,6,7,8-tetrahydro- 5,5,8,8-tetramethyl-2-naphthyl)ethoxy]benzamide:
methyl 2-hydroxy-4-[2-hydroxy-2-(4,4 -dimethylthiochroman-6-yl)ethoxy]benzoate;
2-hydroxy-4-[2-hydroxy-2-(4,4-dimethylthiochroman-6-yl)ethoxy]benzoic acid;
2-hydroxy-4-[3-hydroxy-3-(5,6,7,8-tetrahydro-5,5,8,8-tetramethyl-2-naphthyl)propyl]benzoic acid;
2-hydroxy-4-[2-hydroxy-2-(5,6,7,8-tetrahydro-5,5,8,8-tetramethyl-2-naphthyl)ethoxy]toluene;
methyl 2,6-dihydroxy-4-[2-hydroxy-2-(5,6,7,8-tetrahydro-5,5,8,8-tetramethyl-2-naphthyl)ethoxy]benzoate;
(−) isomer of 2-hydroxy-4-[2-hydroxy-2-(5,6,7,8-tetrahydro-5,5,8,8-tetramethyl-2-naphthyl)ethoxy]benzoic acid;
(+) isomer of 2-hydroxy-4-[2-hydroxy-2-(5,6,7,8-tetrahydro-5,5,8,8-tetramethyl-2-naphthyl)ethoxy]benzoic acid;
2-hydroxy-4-[2-hydroxy-2-(3-methoxy-5,6,7,8-tetrahydro-5,5,8,8-tetramethyl-2-naphthyl)ethoxy[benzoic acid;
2-methoxy-4-[2-hydroxy-2-(5,6,7,8-tetrahydro-5,5,8,8-tetramethyl-2-naphthyl)ethoxy]benzoic acid;
2-hydroxy-4-[2-hydroxy-2-(3-hydroxy-5,6,7,8-tetrahydro-5,5,8,8-tetramethyl-2-naphthyl)ethoxy]benzoic acid;
2-hydroxy-4-[2-amino-2-(5,6,7,8-tetrahydro-5,5,8,8-tetramethyl-2-naphthyl)ethoxy]benzoic acid;
2-hydroxy-4-[2-hydroxy-2-(5,6,7,8-tetrahydro-5,5,8,8-tetramethyl-2-naphthyl)propyloxy]benzoic acid;
2-hydroxy-4-[2-hydroxy-2-(5,6,7,8-tetrahydro-5,5,8,8-tetramethyl-2-naphthyl)hexyloxy[benzoic acid; and
2-hydroxy-4-[2-hydroxy-2-(5,6,7,8-tetrahydro-5,5,8,8-tetramethyl-2-naphthyl)ethylamino]benzoic acid.

14. A pharmaceutical composition, wherein said composition contains at least one compound of formula (I) according to claim 1 in an appropriate vehicle, for administration by the enteral, parenteral, topical or ocular route.

15. A composition according to claim 14, wherein said composition contains 0.001 to approximately 5% by weight of a compound of formula (I).

16. A cosmetic composition for body and hair hygiene, wherein said composition contains at least one compound of formula (I) according to claim 1 in an appropriate cosmetic vehicle.

17. A cosmetic composition according to claim 16, wherein said composition contains the compound of formula (I) at a concentration of between 0.001 and 3% by weight.

18. Method of treatment of dermatological, rheumatic, respiratory or ophthalmological conditions comprising administering to a patient suffering from at least one of said conditions a therapeutically effective amount of a compound of claim 1.

* * * * *